(12) United States Patent
Kim et al.

(10) Patent No.: US 10,276,646 B2
(45) Date of Patent: Apr. 30, 2019

(54) DISPLAY DEVICE

(71) Applicant: Samsung Display Co., Ltd., Yongin-si, Gyeonggi-do (KR)

(72) Inventors: Hun Kim, Seoul (KR); Yong Jin Kim, Cheonan-si (KR); Soon Jung Wang, Suwon-si (KR); Keun Soo Lee, Cheonan-si (KR); Jae Ho Lee, Suwon-si (KR); Kyung Chan Chae, Hwaseong-si (KR)

(73) Assignee: Samsung Display Co., Ltd. (KR)

( * ) Notice: Subject to any disclaimer, the term of this patent is extended or adjusted under 35 U.S.C. 154(b) by 5 days.

(21) Appl. No.: 15/612,811

(22) Filed: Jun. 2, 2017

(65) Prior Publication Data

US 2018/0166525 A1 Jun. 14, 2018

(30) Foreign Application Priority Data

Dec. 8, 2016 (KR) .................. 10-2016-0166618

(51) Int. Cl.
*H01L 23/32* (2006.01)
*H01L 27/32* (2006.01)
*H01L 51/52* (2006.01)

(52) U.S. Cl.
CPC ...... *H01L 27/3276* (2013.01); *H01L 27/3246* (2013.01); *H01L 27/3262* (2013.01); *H01L 51/5253* (2013.01); *H01L 2227/323* (2013.01)

(58) Field of Classification Search
CPC ............. H01L 27/3276; H01L 27/3297; H01L 51/5253
See application file for complete search history.

(56) References Cited

U.S. PATENT DOCUMENTS

| 8,928,018 | B2 | 1/2015 | Ikeda et al. |
| 9,190,630 | B2 | 11/2015 | Kim et al. |
| 2014/0176844 | A1* | 6/2014 | Yanagisawa .......... G02F 1/1309 349/43 |
| 2016/0218165 | A1 | 7/2016 | Park et al. |
| 2016/0225312 | A1* | 8/2016 | Byun ................... G09G 3/3208 |
| 2016/0232826 | A1* | 8/2016 | Cho ....................... G09G 3/006 |
| 2016/0240598 | A1 | 8/2016 | You |
| 2016/0260928 | A1* | 9/2016 | Choi ................... H01L 51/5253 |

(Continued)

FOREIGN PATENT DOCUMENTS

| KR | 10-2012-0092508 | 8/2012 |
| KR | 10-2014-0060152 | 5/2014 |

(Continued)

*Primary Examiner* — Joseph C. Nicely
(74) *Attorney, Agent, or Firm* — Innovation Counsel LLP

(57) ABSTRACT

A display is provided. The display device includes a display area and a non-display area located around the display area; a base layer; an organic light-emitting diode (OLED) that is located on the base layer in the display area; and a first crack detection line that is located on the base layer in the non-display area; wherein the first crack detection line comprises a first line that extends substantially in a first direction along a first edge of the display area, a second line that is separated from the first line and extends substantially in the first direction, and a third line that is connected to an end of the first line and an end of the second line, wherein a cross-sectional shape of the first line in a second direction crossing the first direction is inversely tapered.

26 Claims, 18 Drawing Sheets

(56) References Cited

U.S. PATENT DOCUMENTS

| | | | | |
|---|---|---|---|---|
| 2016/0293078 A1* | 10/2016 | Byun | .................... | G09G 3/006 |
| 2016/0293883 A1* | 10/2016 | Hong | .................. | H01L 27/3258 |
| 2016/0322451 A1* | 11/2016 | Park | .................... | H01L 27/3276 |
| 2016/0351093 A1* | 12/2016 | Kim | .................... | G09G 3/2092 |
| 2017/0117346 A1* | 4/2017 | Kim | .................... | H01L 23/49555 |
| 2017/0287936 A1* | 10/2017 | Kim | .................... | H01L 27/124 |
| 2018/0090517 A1* | 3/2018 | Park | .................... | H01L 27/1244 |
| 2018/0174505 A1* | 6/2018 | Mandlik | .................. | G09G 3/32 |
| 2018/0182274 A1* | 6/2018 | Jung | .................... | G09G 3/006 |

FOREIGN PATENT DOCUMENTS

| | | |
|---|---|---|
| KR | 10-2016-0091529 | 8/2016 |
| KR | 10-2016-0100135 | 8/2016 |

\* cited by examiner

DISPLAY DEVICE

This application claims the benefit of Korean Patent Application No. 10-2016-0166618, filed on Dec. 8, 2016, in the Korean Intellectual Property Office, the disclosure of which is incorporated herein by reference in its entirety.

BACKGROUND

1. Field

The present inventive concept relates to a display device.

2. Description of the Related Art

Recently, partially bent display devices as well as flat display devices have been developed.

In flat display devices or partially bent display devices, cracks may occur due to stress, which may cause malfunction of the display devices. Therefore, it is important to accurately detect cracks.

SUMMARY

Aspects of the inventive concept provide a display device whose cracks can be detected easily and more accurately.

However, aspects of the inventive concept are not restricted to the one set forth herein. The above and other aspects of the inventive concept will become more apparent to one of ordinary skill in the art to which the inventive concept pertains by referencing the detailed description of the inventive concept given below.

According to an aspect of the inventive concept, there is provided a display device. The display device includes a display area and a non-display area located around the display area; a base layer; an organic light-emitting diode (OLED) that is located on the base layer in the display area; and a first crack detection line that is located on the base layer in the non-display area; wherein the first crack detection line comprises a first line that extends substantially in a first direction along a first edge of the display area, a second line that is separated from the first line and extends substantially in the first direction, and a third line that is connected to an end of the first line and an end of the second line, wherein a cross-sectional shape of the first line in a second direction crossing the first direction is inversely tapered.

According to another aspect of the inventive concept, there is provided a display device. The display device includes a display area and a non-display area located around the display area; a base layer; a thin-film transistor that is located on the base layer in the display area; a pad that is located on the base layer in the non-display area; a data line that is located on the base layer, extends substantially in a first direction, is electrically connected to the thin-film transistor in the display area, and is electrically connected to the pad in the non-display area; and a crack detection pattern that is located between an edge of the base layer and the data line in the non-display area and separated from the data line, wherein a cross-sectional shape of the crack detection line in a second direction crossing the first direction is inversely tapered.

BRIEF DESCRIPTION OF THE DRAWINGS

These and/or other aspects will become apparent and more readily appreciated from the following description of the embodiments, taken in conjunction with the accompanying drawings in which.

DETAILED DESCRIPTION

Figure 1:
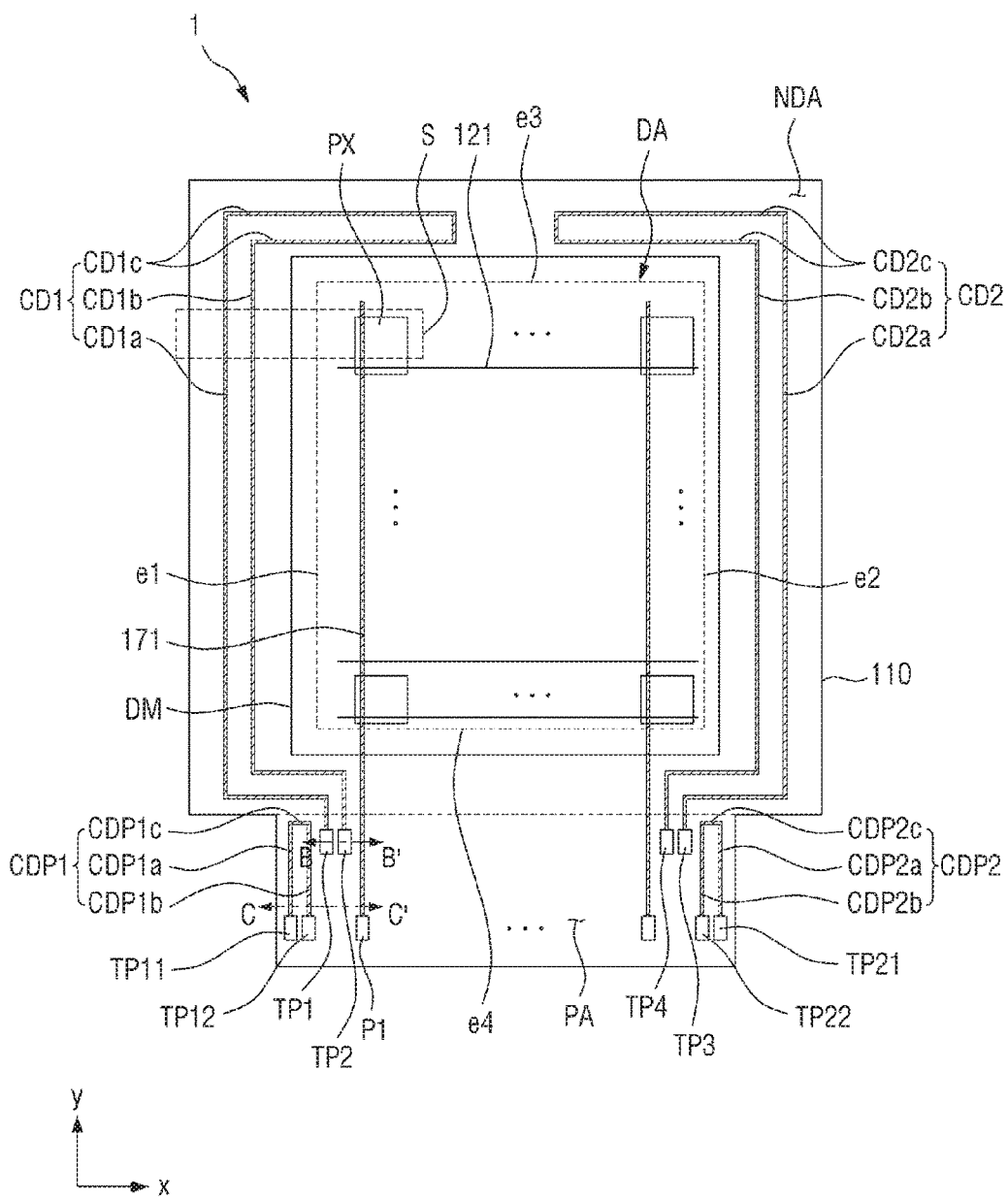
FIG. 1 is a schematic plan view of a display device according to an embodiment.

Features of the inventive concept and methods of accomplishing the same may be understood more readily by reference to the following detailed description of embodiments and the accompanying drawings. The inventive concept may, however, be embodied in many different forms and should not be construed as being limited to the embodiments set forth herein. Rather, these embodiments are provided so that this disclosure will be thorough and complete and will fully convey the concept of the inventive concept to those skilled in the art, and the inventive concept will only be defined by the appended claims. Like reference numerals refer to like elements throughout the specification.

The terminology used herein is for the purpose of describing particular embodiments only and is not intended to be limiting of the inventive concept. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

It will be understood that when an element or layer is referred to as being "on", "connected to" or "coupled to" another element or layer, it may be directly on, connected or coupled to the other element or layer, or intervening elements or layers may be present. In contrast, when an element is referred to as being "directly on", "directly connected to" or "directly coupled to" another element or layer, there are no intervening elements or layers present. As used herein, the term "and/or" includes any and all combinations of one or more of the associated listed items.

It will be understood that, although the terms first, second, etc., may be used herein to describe various elements, components, regions, layers and/or sections, these elements, components, regions, layers and/or sections are not limited by these terms. These terms are only used to distinguish one element, component, region, layer or section from another region, layer or section. Thus, a first element, component, region, layer or section discussed below could be termed a second element, component, region, layer or section without departing from the teachings of the inventive concept.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the exemplary term "below" can encompass both an orientation of above and below. The device may be otherwise oriented (rotated 90 degrees or at other orientations), and the spatially relative descriptors used herein are to be interpreted accordingly.

Unless otherwise defined, all terms (including technical and scientific terms) used herein have the same meaning as commonly understood by one of ordinary skill in the art to which the present application belongs. It will be further understood that terms, such as those defined in commonly used dictionaries, should be interpreted as having a meaning that is consistent with their meaning in the context of the relevant art and this specification and not be interpreted in an idealized or overly formal sense unless expressly so defined herein.

In the following embodiments, the x-axis, the y-axis, and the z-axis are not limited to three axes on an orthogonal coordinate system but may be interpreted in a broad sense, including the three axes. For example, the x-, y-, and z-axes may be orthogonal to each other but may also refer to different directions that are not orthogonal to each other.

Throughout the specification, same or like reference characters in the drawings denote same or like elements.

Hereinafter, embodiments of the inventive concept will be described with reference to the attached drawings.

Figure 2:
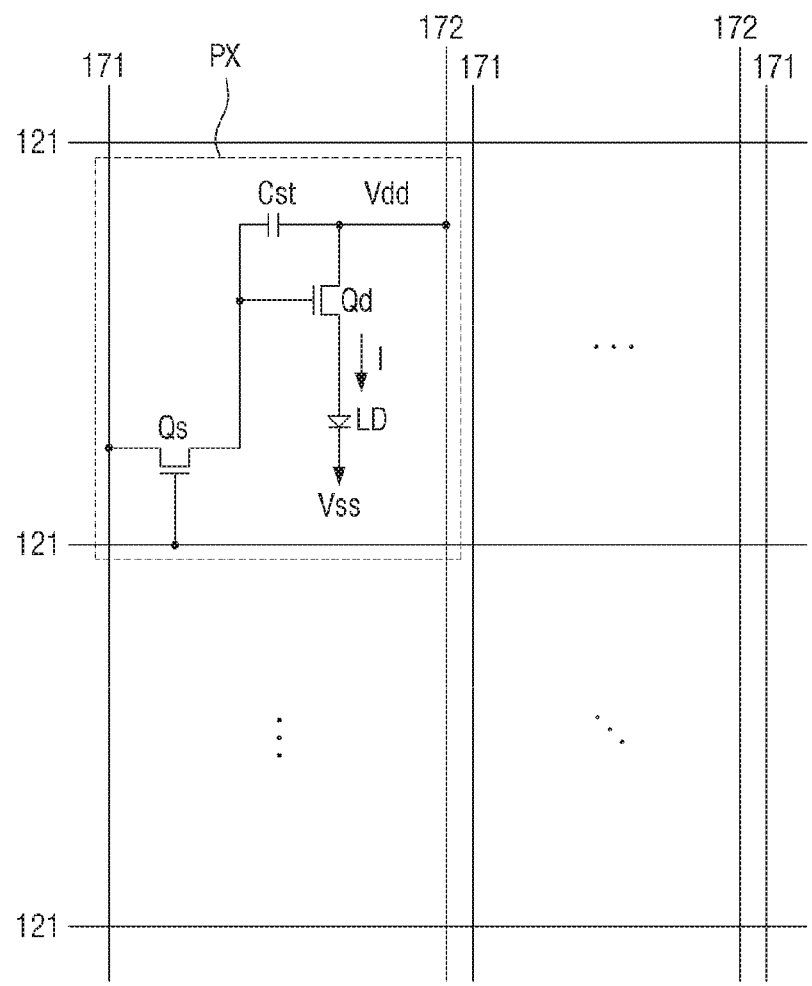
FIG. 2 is an equivalent circuit diagram of one pixel element of the display device according to the embodiment of FIG. 1.
Figure 3:
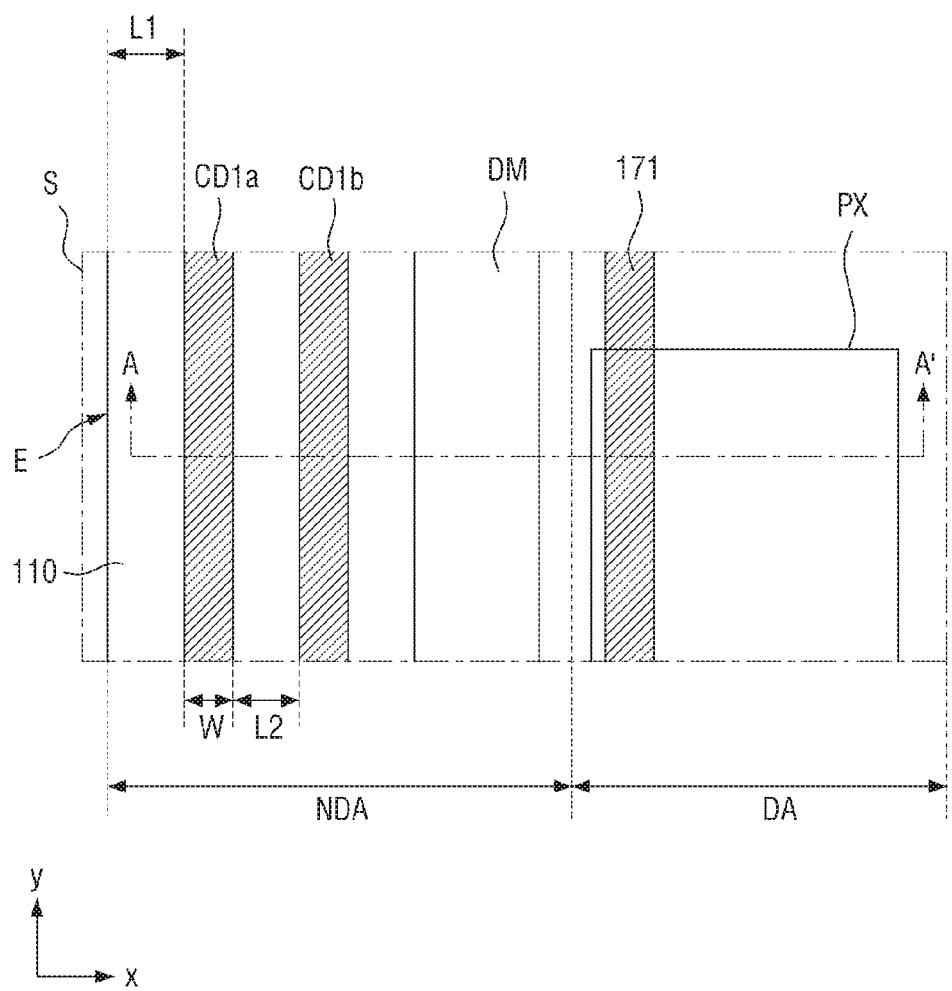
FIG. 3 is an enlarged plan view of a portion 'S' of FIG. 1.

FIG. 1 is a schematic plan view of a display device 1 according to an embodiment. FIG. 2 is an equivalent circuit diagram of one pixel element PX of the display device 1 according to the embodiment of FIG. 1. FIG. 3 is an enlarged plan view of a portion 'S' of FIG. 1.

Referring to FIG. 1, the display device 1 according to the embodiment includes a display area DA in which an image recognizable by a user is displayed and a non-display area NDA which is located around the display area DA. The non-display area NDA includes a pad area PA. The display area DA is an area in which pixel elements PX are disposed to form an image, and the non-display area NDA is an area in which no image is formed. The pad area PA of the non-display area NDA is an area in which pads for transmitting external power and control signals to each element of the display device 1 are located.

If a vertical direction v is referred to as a first direction and a horizontal direction x as a second direction on the basis of the drawing, the display area DA may include a first edge e1 that is located on a left side of the drawing, a second edge e2 that faces the first edge e1 and is located on a right side of the drawing, a third edge e3 that is located between the first edge e1 and the second edge e2 and positioned on an upper side of the drawing, and a fourth edge e4 that faces the third edge e3 and is located on a lower side of the drawing. The pad area PA may be located outside the fourth edge e4 of the display area DA.

A plurality of signal lines (121 and 171) and a pixel element PX are located on a base layer 110 of the display device 1.

The pixel element PX is located in the display area DA and may be provided in a plurality in the display area DA. The pixel element PX denotes a group of elements included in one pixel, which is a minimum unit for displaying an image.

The signal lines (121 and 171) include a gate line 121, which delivers a gate signal or a scan signal and extends in the second direction x, and a data line 171, which delivers a data signal, extends in the first direction y that crosses the second direction x, and is insulated from the gate line 121. The gate line 121 and the data line 171 may be located in the display area DA, and part of the gate line 121 and part of the data line 171 may extend up to the non-display area NDA.

A data pad P1 may be located on the base layer 110 and in the pad area PA. The data pad P1 delivers a data voltage received from an external source to the data line 171. The data pad P1 may be connected to the data line 171 extending to the non-display area NDA, more specifically, to the pad area PA.

Although not illustrated in FIG. 1, a driving voltage line 172 (see FIG. 2) for delivering a driving voltage may further be disposed on the base layer 110 of the display device 1. The driving voltage line 172 may extend substantially parallel to the data line 171.

Referring to FIG. 2, each pixel element PX includes a driving thin-film transistor Qd as a switching element, a switching thin-film transistor Qs as a switching element, a storage capacitor Cst and an organic light-emitting diode (OLED) LD, and further includes part of the gate line 121, part of the data line 171 and part of the driving voltage line 172.

The driving thin-film transistor Qd has a control terminal, an input terminal and an output terminal. The control terminal is connected to the switching thin-film transistor Qs, the input terminal is connected to the driving voltage line 172, which provides a driving voltage Vdd, and the output terminal is connected to the OLED LD. The driving thin-film transistor Qd controls an electric current I supplied to the OLED LD.

The switching thin-film transistor Qs also has a control terminal, an input terminal and an output terminal. The control terminal is connected to the gate line 121, the input terminal is connected to the data line 171, and the output terminal is connected to the control terminal of the driving thin-film transistor Qd. The switching thin-film transistor Qs delivers a data voltage applied to the data line 171 to the driving thin-film transistor Qd in response to a scan signal transmitted to the gate line 121.

The storage capacitor Cst is connected between the control terminal and the input terminal of the driving thin-film transistor Qd. The storage capacitor Cst is charged with a data voltage applied to the control terminal of the driving thin-film transistor Qd and maintains the charged data voltage for a predetermined period even after the switching thin-film transistor Qs is turned off.

The OLED LD includes an anode, which is connected to the output terminal of the driving thin-film transistor Qd, a cathode, which is connected to a common voltage line providing a common voltage Vss, and an organic light-emitting layer. The OLED LD emits light with different intensity according to the electric current I output from the driving thin-film transistor Qd so as to display an image.

In the embodiment described above, in relation to each of the switching thin-film transistor Qs and the driving thin-film transistor Qd, the control terminal may be a gate electrode, the input terminal may be any one of a source electrode and a drain electrode, and the output terminal may be the other one of the source electrode and the drain electrode. For example, when the input terminal is a source electrode, the output terminal may be a drain electrode.

Referring back to FIG. 1, a first crack detection line CD1 may be located on the base layer 110 of the display device 1. The first crack detection line CD1 may be located in the non-display area NDA.

The first crack detection line CD1 may be located in the non-display area NDA outside the first edge e1 of the display area DA.

The first crack detection line CD1 may include a first line CD1a that extends substantially in the first direction y along the first edge e1 of the display area DA, a second line CD1b that is separated from the first line CD1a and extends substantially in the first direction y, and a third line CD1c that connects an end of the first line CD1a and an end of the second line CD1b.

The first line CD1a and the second line CD1b may be located in the non-display area NDA outside a left side of the display area DA. In some embodiments, the third line CD1c may be located outside an upper side of the display area DA or located in the non-display area NDA outside the third edge e3 of the display area DA as illustrated in FIG. 1.

A cross-sectional shape of the first line CD1a in the second direction x may be inversely tapered. In some embodiments, a cross-sectional shape of the second line CD1b in the second direction x may also be inversely tapered. Also, in some embodiments, a cross-sectional shape of the third line CD1c in the first direction y may be inversely tapered. When a crack is generated in the non-display area NDA of the display device 1, it may be transmitted to the first crack detection line CD1, thus partially damaging or breaking the first crack detection line CD1. In particular, when the cross-sectional shape of at least any one of the first line CD1a and the second line CD1b is inversely tapered, for example, has a smaller lower width than an upper width, the first crack detection line CD1 can be more easily damaged or broken by the crack. Therefore, cracks in the display device 1 can be easily detected, thereby preventing defects of the display device 1 due to cracks.

Referring to FIG. 3, the first crack detection line CD1 may be spaced apart from an edge E of the base layer 110 by a predetermined distance. This is to prevent the first crack detection line CD1 from being damaged in the process of cutting a mother substrate during the process of manufacturing a display device. In some embodiments, a shortest gap or distance L1 between the first crack detection line CD1 and the edge E of the base layer 110 may be 50 to 100 μm.

In some embodiments, a line width W of the first line CD1a. i.e., a width of the first line CD1a measured along the second direction x, may be in a range of 5 to 10 μm. Similarly, a line width of the second line CD1b may also be in a range of 5 to 10 μm.

In some embodiments, a distance L2 between the first line CD1a and the second line CD1b measured along the second direction x may be in a range of 15 to 20 μm.

Referring back to FIG. 1, like the first crack detection line CD1, a second crack detection line CD2 may be located on the base layer 110 of the display device 1. The second crack detection line CD2 may be located in the non-display area NDA of the display device 1. The second crack detection line CD2 may be located in the non-display area NDA outside the second edge e2 of the display area DA.

The second crack detection line CD2 may include a fourth line CD2a that extends substantially in the first direction y along the second edge e2 of the display area DA, a fifth line CD2b that is separated from the fourth line CD2a and extends substantially in the first direction y, and a sixth line CD2c that connects an end of the fourth line CD2a and an end of the fifth line CD2b. A cross-sectional shape of the fourth line CD2a in the second direction x may be inversely tapered. In some embodiments, a cross-sectional shape of the fifth line CD2b in the second direction x may also be inversely tapered. Also, in some embodiments, a cross-sectional shape of the sixth line CD2c in the first direction y may be inversely tapered.

That is, the first and second crack detection lines CD1 and CD2 are formed in the non-display area NDA adjacent to both edges of the display area DA and are formed in the shape of a hemiring.

However, the shape of each of the first and second crack sensing lines CD1 and CD2 is not limited to the shape in the above embodiment. For example, the first crack detection line CD1 may further include a line extending along the first direction y in addition to the first line CD1a and the second line CD1b. In this case, a connector that connects the second line CD1b and the additional line may be further included in the first crack detection line CD1. Similarly, the second crack detection line CD2 may further include an additional line and a connector in addition to the fourth line CD2a and the fifth line CD2b.

First through fourth test pads TP through TP4 may be positioned in the pad area PA. The first test pad TP1 and the second test pad P2 transmit test signals for detecting cracks to the first crack detection line CD1. An end of the first line CD1a may extend up to the pad area PA to be connected to the first test pad TP1, and an end of the second line CD1b may extend up to the pad region PA to be connected to the second test pad TP2.

There is a high probability that no crack will occur in the display device 1 before the process of cutting a mother substrate or before the process of bending part of the display device 1. When a crack is generated in the display device 1 and damage is done to the first crack detection line CD1, a resistance value of the first crack detection line CD1 may increase, and the first crack detection line CD1 may be partially broken.

Therefore, a voltage is applied to the first test pad TP1 and the second test pad TP2 before the cutting process or the bending process to obtain a first test value (e.g., an electric current value), the voltage is applied to the first test pad TP1 and the second test pad TP2 after the cutting process or the bending process to obtain a second test value (e.g., an electric current value), and the first test value and the second test value are compared to determine whether a crack has occurred in the display device 1.

However, the above-described crack detection process is merely an example, and whether a crack has occurred in the display device 1 can be detected in various ways using the first crack detection line CD1.

Like the first test pad TP1 and the second test pad TP2, the third test pad TP3 and the fourth test pad TP4 transmit test signals for detecting cracks to the second crack detection line CD2. An end of the fourth line CD2a may extend up to the pad area PA to be connected to the third test pad TP3, and an end of the fifth line CD2b may extend up to the pad region PA to be connected to the fourth test pad TP4.

A first crack detection pattern CDP1 for detecting cracks in the pad area PA may be located in the pad area PA. The first crack detection pattern CDP1 may be separated from the data line 171 located in the pad area PA and may be disposed between a left edge of the base layer 110 and a leftmost data line 171.

In some embodiments, the first crack detection pattern CDP1 may include a first pattern CDP1a that extends in the first direction y, a second pattern CDP1b that is separated from the first pattern CDP1a and extends in the first direction y, and a first connection pattern CDP1c that connects the first pattern CDP1a and the second pattern CDP1b.

In some embodiments, a cross-sectional shape of the first pattern CDP1a in the second direction x may be inversely tapered, and a cross-sectional shape of the second pattern CDP1b in the second direction x may also be inversely tapered. Accordingly, cracks occurring in the pad area PA of the display device 1 can be easily detected.

A second crack detection pattern CDP2 may further be provided on the opposite side of the pad area PA to the first crack detection pattern CDP1. The second crack detection pattern CDP2 may be separated from the data line 171 located in the pad area PA and may be disposed between a right edge of the base layer 110 and a rightmost data line 171.

In some embodiments, like the first crack detection pattern CDP1, the second crack detection pattern CDP2 may include a third pattern CDP2a that extends in the first direction y, a fourth pattern CDP2b that is separated from the third pattern CDP2a and extends in the first direction y, and a second connection pattern CDP2c that connects the third pattern CDP2a and the fourth pattern CDP2b. In some embodiments, a cross-sectional shape of the third pattern CDP2a in the second direction x may be inversely tapered, and a cross-sectional shape of the fourth pattern CDP2b in the second direction x may also be inversely tapered.

A fifth test pad TP11, a sixth test pad TP12, a seventh test pad TP21 and an eighth test pad TP22 to which test signals for detecting cracks are transmitted are located on the base layer 110 in the pad area PA. The fifth test pad TP11 may be connected to the first pattern CDP1a, the sixth test pad TP12 may be connected to the second pattern CDP1b, the seventh test pad TP21 may be connected to the third pattern CDP2a, and the eighth test pad TP22 may be connected to the fourth pattern CDP2b. The crack detection process is the same as or similar to that described above in the description of the first crack detection line CD1, and thus a description of the crack detection process is omitted.

A dam DM may be located on the base layer 110 in the non-display area NDA in order to prevent organic matter located in the display area DA from flowing over the edge of the base layer 110. In FIG. 1, one dam DM is illustrated as an example. However, in some other embodiments, two or more dams DM may be formed.

The dam DM may surround the display area DA and may be located between the first and second crack detection lines CD1 and CD2 and the display area DA. In other words, the first crack detection line CD1 and the second crack detection line CD2 may be located relatively further from the center than the dam DM.

The layer structure of the display device 1 according to the embodiment will hereinafter be described in detail with reference to the drawings. Since the switching thin-film transistor Qs and the driving thin-film transistor Qd of each pixel element PX have the same layer structure, the layer structure of the display device 1 will be described in detail according to a stacking sequence, focusing mainly on the driving thin-film transistor Qd and the OLED LD of the pixel element PX. A driver circuit for driving the pixel element PX may also be formed in the non-display area NDA of the display device 1. Since the driver circuit includes a plurality of signal lines and a plurality of thin-film transistors, one circuit thin-film transistor Ts will be described as an example. In the following description, elements and features identical to those described above will be mentioned briefly or omitted.

Figure 4:
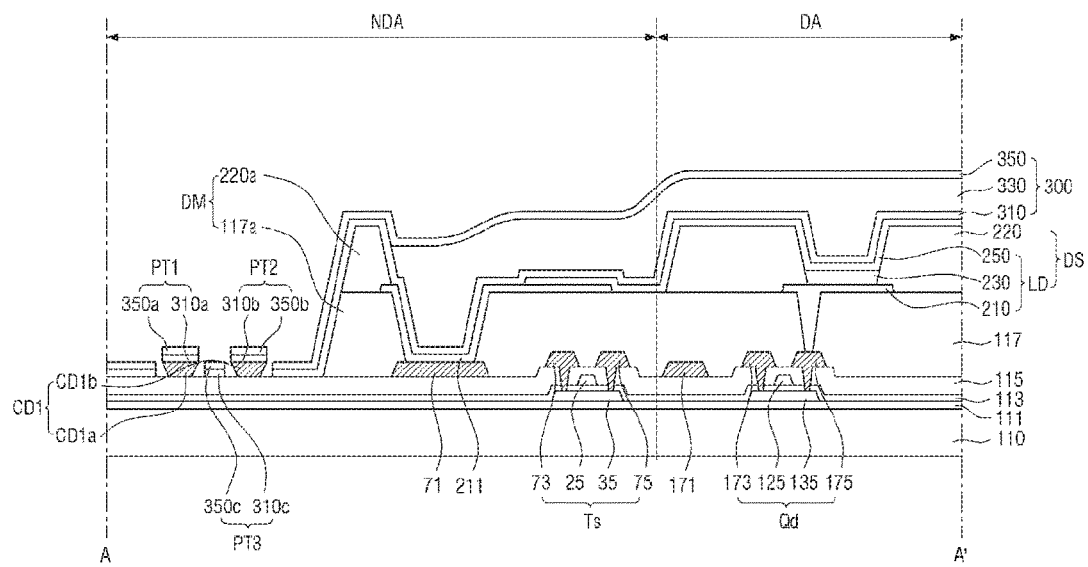
FIG. 4 is a cross-sectional view taken along the line A-A' of FIG. 3.
Figure 5:
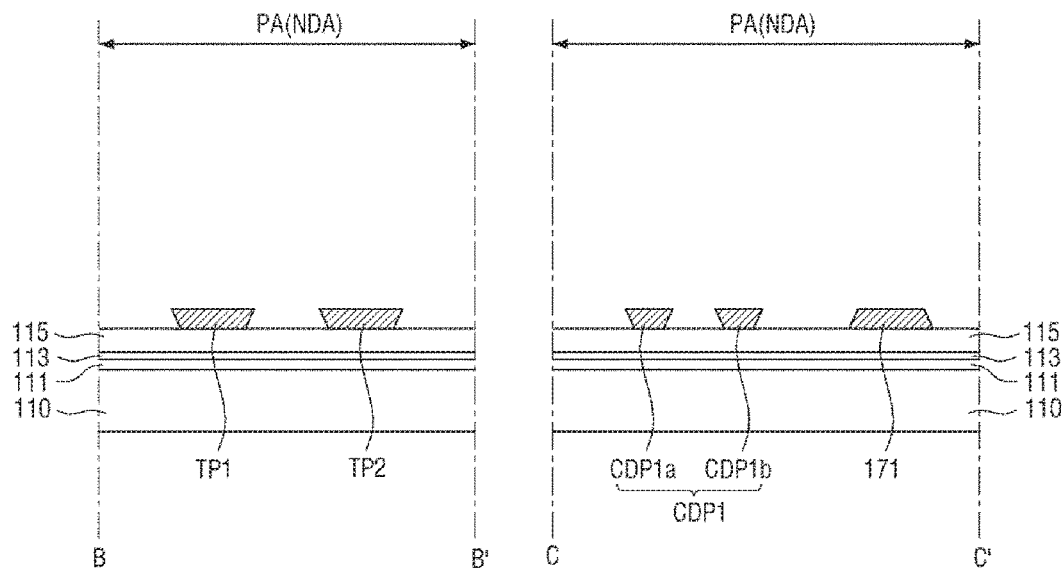
FIG. 5 is a cross-sectional view taken along the lines B-B' and C-C' of FIG. 1.

FIG. 4 is a cross-sectional view taken along the line A-A' of FIG. 3. FIG. 5 is a cross-sectional view taken along the lines B-B' and C-C' of FIG. 1.

Referring to FIGS. 1 and 3 through 5, the base layer 110 of the display device 1 may be made of transparent resin. For example, the base layer 110 may include polymethylmethacrylate resin, polyimide resin, acrylic resin, polyacrylate resin, polycarbonate resin, polyether resin, sulfonic acid resin, polyethylene terephthalate resin, etc. The base layer 110 may be a transparent flexible substrate having flexibility such as elasticity. That is, the base layer 110 is foldable, bendable, rollable, or stretchable in at least one direction. In an embodiment, the base layer 110 may be a transparent ceramic substrate such as a glass substrate, a quartz substrate or a transparent alumina substrate.

A buffer layer 111 may be located on the base layer 110. The buffer layer 111 may be made of a silicon compound, transparent resin, or the like. For example, the buffer layer 111 may include at least one buffer film that contains silicon oxide, silicon nitride, silicon oxycarbide, silicon carbonitride, polyacrylate resin, polymethacrylate resin, olefin resin and/or polyvinyl resin. According to embodiments, the buffer layer 111 may include two buffer films made of different silicon compounds. Alternatively, the buffer layer 111 may have a structure in which at least one buffer film containing a silicon compound and at least one buffer film containing transparent resin are stacked substantially alternately. However, the structure of the buffer layer 111 may vary depending on the configuration, dimensions, use, etc., of the display device 1. The buffer layer 120 may prevent penetration of unnecessary components such as impurities, metal atoms and moisture. In addition, the buffer layer 111 may planarize the surface of the base layer 110.

A semiconductor layer 135 of the driving thin-film transistor Qd and a semiconductor layer 35 of the circuit thin-film transistor Ts may be located on the buffer layer 111. Each of the semiconductor layers 35 and 135 may be made of poly silicon, an oxide semiconductor, or the like. The oxide semiconductor may include at least one of an oxide of titanium (Ti), hafnium (Hf), zirconium (Zr), aluminum (Al), tantalum (Ta), germanium (Ge), zinc (Zn), gallium (Ga), tin (Sn) or indium (In) and composite oxides of these materials such as indium-gallium-zinc oxide (InGaZnO4), indium-zinc oxide (In—Zn—O), zinc-tin oxide (Zn—Sn—O) indium-gallium oxide (In—Ga—O), indium-tin oxide (In—Sn—O), indium-zirconium oxide (In—Zr—O), indium-zirconium-zinc oxide (In—Zr—Zn—O), indium-zirconium-tin oxide (In—Zr—Sn—O), indium-zirconium-gallium oxide (In—Zr—Ga—O), indium-aluminum oxide (In—Al—O), indium-zinc-aluminum oxide (In—Zn—Al—O), indium-tin-aluminum oxide (In—Sn—Al—O), indium-aluminum-gallium oxide (In—Al—Ga—O), indium-tantalum oxide (In—Ta—O), indium-tantalum-zinc oxide (In—Ta—Zn—O), indium-tantalum-tin oxide (In—Ta—Sn—O), indium-tantalum-gallium oxide (In—Ta—Ga—O), indium-germanium oxide (In—Ge—O), indium-germanium-zinc oxide (In—Ge—Zn—O), indium-germanium-tin oxide (In—Ge—Sn—O), indium-germanium-gallium oxide (In—Ge—Ga—O), titanium-indium-zinc oxide (Ti—In—Zn—O) and hafnium-indium-zinc oxide (Hf—In—Zn—O). When the semiconductor layers 35 and 135 are made of an oxide semiconductor, a protective layer may be added to protect the oxide semiconductor, which is vulnerable to external environments such as high temperatures.

A gate insulating layer 113, which covers the semiconductor layers 35 and 135, may be disposed on the buffer layer 111. The gate insulating layer 113 may be made of a silicon compound such as silicon oxide or silicon carbide. Alternatively, the gate insulating layer 113 may be made of a metal oxide such as hafnium oxide, aluminum oxide, zirconium oxide, titanium oxide or tantalum oxide.

Gate electrodes 25 and 125 may be located on the gate insulating layer 113 and may overlap the semiconductor layers 35 and 135. Each of the gate electrodes 25 and 125 may be a single layer or a multilayer made of a low-resistance material or a highly corrosive material such as Al, Ti, Mo, Cu, Ni. or an alloy of these materials.

A first interlayer insulating film 115, which covers the gate electrodes 25 and 125, may be disposed on the gate insulating layer 113. The first interlayer insulating film 115 may separate the gate electrode 25 of the circuit thin-film transistor Ts and the gate electrode 125 of the driving thin-film transistor Qd from wiring layers and/or electrodes disposed on the gate electrodes 25 and 125. The first interlayer insulating film 115 may include a silicon compound, transparent resin, or the like. For example, the first interlayer insulating film 115 may include silicon oxide, silicon nitride, silicon oxynitride, silicon carbonitride, silicon oxycarbide, polyacrylate resin, polymethacrylate resin, olefin resin, polyvinyl resin, or the like.

A power supply line 71, the data line 171, source electrodes 73 and 173, and drain electrodes 75 and 175 may be located on the first interlayer insulating film 115. In some embodiments, the power supply line 71 may be the common voltage line to which the common voltage Vss (see FIG. 2) described above with reference to FIG. 2 is applied.

The source electrode 73 and the drain electrode 75 of the circuit thin-film transistor Ts may be electrically connected to the semiconductor layer 35 of the circuit thin-film transistor Ts through contact holes formed in the first interlayer insulating film 115 and the gate insulating layer 113.

The source electrode 173 and the drain electrode 175 of the driving thin-film transistor Qd may be connected to the semiconductor layer 135 of the driving thin-film transistor Qd through contact holes formed in the first interlayer insulating film 115 and the gate insulating layer 113.

Each of the power supply line 71, the data line 171, the source electrodes 73 and 173 and the drain electrodes 75 and 175 may be a single layer or a multilayer made of a low-resistance material or a highly corrosive material such as Al, Ti, Mo, Cu, Ni, or an alloy of these materials. For example, the multilayer may be a triple layer of Ti/Cu/Ti, Ti/Ag/Ti, or Mo/Al/Mo.

The semiconductor layer 135, the gate electrode 125, the source electrode 173 and the drain electrode 175 located in the display area DA form the driving thin-film transistor Qd serving as a switching element. Similarly, the semiconductor layer 35, the gate electrode 25, the source electrode 73 and the drain electrode 75 located in the non-display area NDA form the circuit thin-film transistor Ts serving as a switching element.

A second interlayer insulating film 117, which covers the driving thin-film transistor Qd and the data line 171 of the display area DA, may be located on the first interlayer insulating film 115. The second interlayer insulating film 117 may cover the circuit thin-film transistor Ts and extend up to the non-display area NDA to partially cover the power supply line 71.

The second interlayer insulating film 117 may be made of an organic material. For example, the second interlayer insulating film 117 may include polyimide resin, photoresist, acrylic resin, polyamide resin, siloxane resin, or the like. These materials may be used alone or in combination with each other. In other embodiments, the second interlayer insulating film 117 may be made of an inorganic material such as a silicon compound, a metal oxide, or the like. For example, the second interlayer insulating film 117 may include silicon oxide, silicon nitride, silicon oxynitride, silicon oxycarbide, silicon carbonitride, aluminum oxide, titanium oxide, tantalum oxide, magnesium oxide, zinc oxide, hafnium oxide, zirconium oxide, titanium oxide, or the like.

A connection electrode 211 and a first electrode 210 may be located on the second interlayer insulating film 117. The first electrode 210 may be electrically connected to the drain electrode 175 of the driving thin-film transistor Qd through a contact hole formed in the second interlayer insulating film 117. The first electrode 210 may be the anode of the OLED LD.

The connection electrode 211 and the first electrode 210 may be made of the same material. In an example, each of the connection electrode 211 and the first electrode 210 may include a reflective film made of Ag, Mg, Al, Pt, Pd, Au, Ni, Nd, Ir, Cr or a compound of these materials and a transparent or translucent electrode layer formed on the reflective film. The transparent or translucent electrode layer may include at least one of indium tin oxide (ITO), indium zinc oxide (IZO), zinc oxide (ZnO), indium oxide ($In_2O_3$), indium gallium oxide (IGO), and aluminum zinc oxide (AZO).

The connection electrode 211 may be connected to the power supply line 71 and may contact the power supply line 71.

A pixel defining layer 220 may be disposed on the second interlayer insulating film 117 in the display area DA. The pixel defining layer 220 may include an opening that exposes the first electrode 210. In some embodiments, the pixel defining layer 220 may extend on part of the second interlayer insulating film 117 to overlap the data line 171 located in the display area DA. The pixel defining layer 220 may include an organic material. For example, the pixel defining layer 220 may contain polyimide resin, photoresist, polyacrylic resin, polyamide resin, acrylic resin, or the like.

A light emitting layer 230 may be disposed on the first electrode 210, which is exposed by the opening of the pixel defining layer 220. The light emitting layer 230 may have a multilayer structure including an organic light emitting layer (EL), a hole injection layer (HIL), a hole transport layer (HTL), an electron transport layer (ETL), and an electron injection layer (EIL). In some embodiments, the organic light emitting layer of the light emitting layer 230 may include a light emitting material capable of generating light of different colors, such as red light, green light, and blue light, according to the pixel type of the display device 1. In other embodiments, the organic light emitting layer of the light emitting layer 230 may include a stack of a plurality of light emitting materials capable of generating light of different colors such as red light, green light and blue light. Consequently, white light may be emitted from the organic light emitting layer of the light emitting layer 230.

A second electrode 250 may be disposed on the light emitting layer 230 and the pixel defining layer 220. The second electrode 250 may be the cathode. The second electrode 250 may extend to the non-display area NDA and may contact the connection electrode 211. Accordingly, the common voltage Vss (see FIG. 2) provided to the power supply line 71 may be provided to the second electrode 250 through the connection electrode 211. The second electrode 250 may be made of a metal, an alloy, a metal nitride, a conductive metal oxide, a transparent conductive material, or the like.

The first electrode 210, the light emitting layer 230 and the second electrode 250 form the OLED LD. The OLED LD and the pixel defining layer 220 may form a display structure DS.

As described above with reference to FIG. 1, the dam DM may be located in the non-display area NDA of the display device 1. The dam DM may prevent an organic film 330 of a thin-film encapsulation layer 300, which will be described later, from spreading non-ideally to the edge of the display device 1.

The dam DM may be located relatively further from the center than the power line 71. In other words, a distance between the dam DM and the display area DA may be greater than a distance between the power supply line 71 and the display area DA. That is, the power supply line 71 may be positioned between the dam DM and the display area DA.

In some embodiments, the dam DM may include a first pattern 117a that is located on the first interlayer insulating film 115 and a second pattern 220a that is located on the first pattern 117a. In an example, the first pattern 117a may be made of the same material as the second interlayer insulating film 117, and the second pattern 220a may be made of the same material as the pixel defining layer 220.

In some embodiments, the dam DM may partially overlap the power supply line 71 and may be separated from the second interlayer insulating film 117 with the power supply line 71 interposed between them. The dam DM made of the same material as at least any one of the second interlayer insulating film 117 and the pixel defining layer 220 may have good bonding strength with metal. Therefore, if the dam DM is formed to contact the power supply line 71 made of a metal material, the dam DM can be stably formed to have excellent bonding strength.

The first crack detection line CD1 may be located in the non-display area NDA of the display device 1. The first crack detection line CD1 may include the first line CD1a and the second line CD1b. The first crack detection line CD1 may be located relatively further from the center than the dam DM and the power supply line 71. In other words, a distance between the first crack detection line CD1 and the display area DA may be greater than the distance between the dam DM and the display area DA and the distance between the power supply line 71 and the display area DA.

That is, the dam DM and the power supply line 71 may be located between the first crack detection line CD1 and the display area DA.

The first crack detection line CD1 may be formed on the same layer and of the same material as the power supply line 71, the data line 171, the source electrodes 73 and 173 and the drain electrodes 75 and 175.

The thin-film encapsulation layer 300 for sealing the display structure DS may be disposed on the display structure DS of the display area DA. The thin-film encapsulation layer 300 may also be disposed in part of the non-display area NDA.

The thin-film encapsulation layer 300 may include one or more organic films and one or more inorganic films. In some embodiments, the thin-film encapsulation layer 300 may include at least one sandwich structure in which at least one organic film is interposed between at least two inorganic films. The thin-film encapsulation layer 300 including a first inorganic film 310, a second inorganic film 350 and the organic film 330 disposed between the first inorganic film 310 and the second inorganic film 350 will hereinafter be described as an example of the thin-film encapsulation layer 300.

The first inorganic film 310 may be positioned on the second electrode 250 in the display area DA. In the non-display area NDA, the first inorganic film 310 may cover the connection electrode 211 and the dam DM. In some embodiments, the first inorganic film 310 may contact the first interlayer insulating film 115 on the outside of the dam DM. The first inorganic film 310 may prevent the display structure DS from deteriorating due to penetration of moisture, oxygen, and the like. The first inorganic film 310 may be made of silicon nitride, aluminum nitride, zirconium nitride, titanium nitride, hafnium nitride, tantalum nitride, silicon oxide, aluminum oxide, titanium oxide, tin oxide, cerium oxide, silicon oxynitride (SiON), or the like.

The organic film 330 may be located on the first inorganic film 310. The organic film 330 may improve the flatness of the display device 1 and protect the display structure DS in the display area DA. The organic film 330 may be made of a liquid organic material such as acrylic resin, methacrylic resin, polyisoprene, vinyl resin, epoxy resin, urethane resin, cellulose resin or perylene resin. This organic material may be provided on the base layer 110 through deposition, printing or coating and may be subjected to a curing process. When the organic material in a liquid state is cured in a state in which it is spread wider than an inorganic film, shrinkage occurs due to moisture permeation. In the current embodiment, the dam DM for preventing the spread of the liquid organic material is provided to control the non-ideal spread of the organic material.

As described above, the spread of the organic film 330 can be controlled by the dam DM. Accordingly, the area of the organic film 330 may be smaller than the area of the first inorganic film 310. In some embodiments, the organic film 330 may be located inside the dam DM. In other words, in some embodiments, the organic film 330 may be located only in the display area DA and in a region of the non-display area NDA between the display area DA and the dam DM.

The second inorganic film 350 may be located on the organic film 330. The second inorganic film 350 may have substantially the same or similar role as the first inorganic film 310 and may be made of substantially the same or similar material as the first inorganic film 310. The second inorganic film 350 may completely cover the organic film 330. The second inorganic film 350 may be located on the first inorganic film 310, which covers the dam DM and contacts the first interlayer insulating film 115 on the outside of the dam DM. Accordingly, the first inorganic film 310 and the second inorganic film 350 may contact each other on an upper side of the dam DM or on the outside of the dam DM.

A first inorganic film pattern PT1 including a first lower inorganic film pattern 310a and a first upper inorganic film pattern 350a may be located on the first line CD1a. In addition, a second inorganic film pattern PT2 including a second lower inorganic film pattern 310b and a second upper inorganic film pattern 350b may be located on the second line CD1b. A third inorganic film pattern PT3 disposed on the first interlayer insulating film 115 may be located between the first line CD1a and the second line CD2a. The third inorganic film pattern PT3 may include a third lower inorganic film pattern 310c and a third upper inorganic film pattern 350c. The first inorganic film pattern PT1 and the second inorganic film pattern PT2 may be separated from the first inorganic film 310 and the second inorganic film 350 of the thin-film encapsulation layer 300. In addition, the first inorganic film pattern PT1 and the second inorganic film pattern PT2 may be separated from the third inorganic film pattern PT3.

The first lower inorganic film pattern 310a, the second lower inorganic film pattern 310b and the third lower inorganic film pattern 310c may be made of the same material as the first inorganic film 310 of the thin-film encapsulation layer 300. The first upper inorganic film pattern 350a, the second upper inorganic film pattern 350b and the third upper inorganic film pattern 350c may be made of the same material as the second inorganic film 350 of the thin-film encapsulation layer 300.

A first inorganic material may be deposited on the first line CD1a and the second line CD1b when it is deposited to form the first inorganic film 310 of the thin-film encapsulation layer 300. The first inorganic material may also be deposited in a space between the first line CD1a and the second line CD1b. Likewise, a second inorganic material may be deposited on the first line CD1a and the second line CD1b when it is deposited to form the second inorganic film 350 of the thin-film encapsulation layer 300. The second inorganic material may also be deposited in a space between the first line CD1a and the second line CD1b.

As described above, the cross-sectional shape of the first line CD1a in the second direction x may have the smaller lower width than the upper width, that is, may be inversely tapered. In some embodiments, the cross-sectional shape of the second line CD1b in the second direction x may also be inverted tapered. Therefore, the first lower inorganic film pattern 310a and the second lower inorganic film pattern 310b formed by depositing the first inorganic material on the first line CD1a and the second line CD1b may be separated from the third lower inorganic film pattern 310c and the first inorganic film 310. Similarly, the first upper inorganic film pattern 350a and the second upper inorganic film pattern 350b formed on the first lower inorganic film pattern 310a and the second lower inorganic film pattern 310b may be separated from the third upper inorganic film pattern 350c and the second inorganic film 350.

When the cross-sectional shape of each of the first line CD1a and the second line CD1b is tapered, for example, has a wider lower surface than an upper surface, even if a crack occurs in the non-display area NDA, there is a high probability that the crack will not be transmitted to the first crack detection line CD1. For example, the first crack detection line CD1 is highly likely to be not damaged or damaged only slightly, and it is difficult for the first crack detection line CD1 to be broken.

On the other hand, according to the current embodiment, the cross-sectional shape of each of the first line CD1a and the second line CD1b is inversely tapered. Therefore, the first crack detection line CD1 can be more easily damaged or broken by a crack generated in the non-display area NDA. Accordingly, cracks in the display device 1 can be easily detected, thereby preventing defects of the display device 1 due to cracks.

In FIG. 4, the cross-sectional shape of each of the first line CD1a and the second line CD1b has a flat inclined surface and is monotonously reduced in width toward the base layer 110 or the first interlayer insulating film 115, but the inventive concept is not limited to this example.

Figure 28:
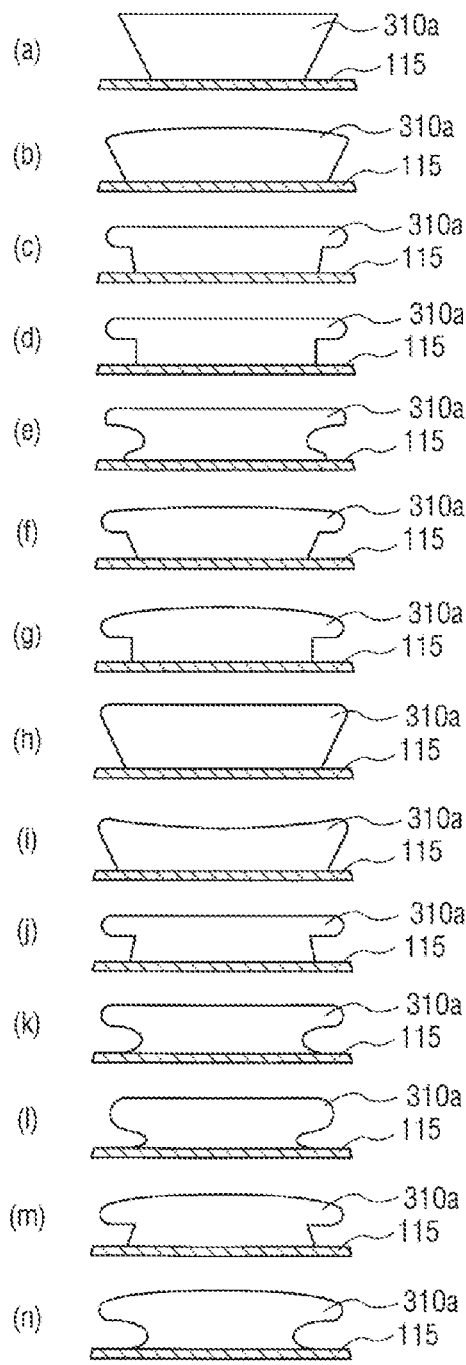
FIG. 28 is a cross-sectional view of modified examples of a cross-sectional shape of a first line of a first crack detection line illustrated in FIG. 4.

FIG. 28 is a cross-sectional view of modified examples of the cross-sectional shape of the first line CD1a of the first crack detection line CD1 in the display device 1 according to the embodiment. As illustrated in (a) through (n) of FIG. 28, the cross-sectional shape of the first line CD1a may have a curved inclined surface or may be reduced in width in stages. Like the cross-sectional shape of the first line CD1a the cross-sectional shape of the second line CD1b may also be variously modified.

Referring back to FIGS. 1 and 3 through 5, in some embodiments, like the cross-sectional shape of the first crack detection line CD1, a cross-sectional shape of each of the first test pad TP1 and the second test pad TP2 located in the pad area PA of the non-display area NDA may be inversely tapered. The first test pad TP1 and the second test pad TP2 may be formed by the same process as that for the first crack detection line CD1. Therefore, when the first crack detection line CD1 is formed to have an inversely tapered cross-sectional shape, each of the first test pad TP1 and the second test pad TP2 may also be formed to have an inversely tapered cross-sectional shape.

Although not illustrated in the drawings, like the cross-sectional shape of the first crack detection line CD1, a cross-sectional shape of at least any one of the fourth line CD2a and the fifth line CD2b of the second crack detection line CD2 in the second direction x may be inversely tapered. In some embodiments, a cross-sectional shape of each of the third test pad TP3 and the fourth test pad TP4 may also be inversely tapered.

In addition, the cross-sectional shape of at least any one of the first pattern CDP1a and the second pattern CDP1b of the first crack detection pattern CDP1 in the second direction x may be inversely tapered as described above. Thus, cracks occurring in the pad area PA can be more easily detected.

Although not illustrated in the drawings, like the cross-sectional shape of the first crack detection pattern CDP1, the cross-sectional shape of at least any one of the third pattern CDP2a and the fourth pattern CDP2b of the second crack detection pattern CDP2 in the second direction x may be inversely tapered.

In some embodiments, the thin-film encapsulation layer 300 may not be disposed in the pad area PA of the non-display area NDA. Accordingly, the thin-film encapsulation layer 300 may not be located on the first test pad TP1 and the second test pad TP2 located in the pad area PA. Therefore, the first test pad TP1 and the second test pad TP2 may not contact nor overlap the thin-film encapsulation layer 300. Likewise, the first and second crack detection patterns CDP1 and CDP2 may not contact the thin-film encapsulation layer 300. In addition, the fifth test pad TP11, the sixth test pad TP12, the seventh test pad TP21 and the eighth test pad TP22 may not contact nor overlap the thin-film encapsulation layer 300.

FIGS. 6 through 13 are cross-sectional views illustrating the process of manufacturing the portion of FIG. 4.

Figure 6:
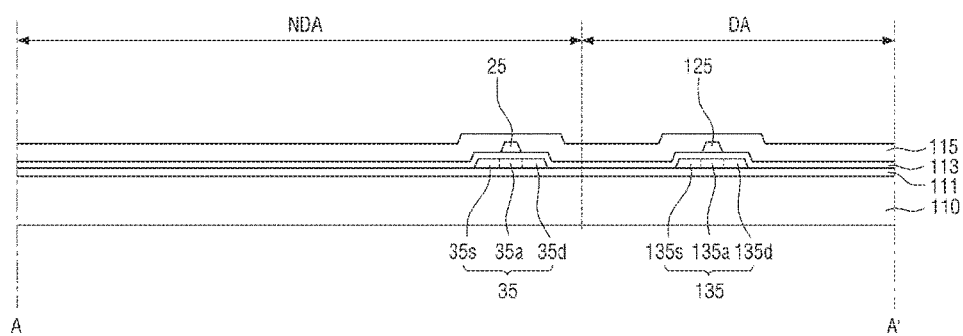
FIGS. 6, 7, 8, 9, 10, 11, 12 and 13 are cross-sectional views illustrating the process of manufacturing the portion of FIG. 4.

Referring to FIGS. 4 and 6 through 13, a buffer layer 111 is formed on a base layer 110 as illustrated in FIG. 6. Then, semiconductor layers 35 and 135 are formed on the buffer layer 111. The semiconductor layers 35 and 135 respectively include source portions 35s and 135s doped with a high concentration impurity, drain portions 35d and 135d, and channel portions 35a and 135a located between the source portions 35s and 135s and the drain portions 35d and 135d.

Next, a gate insulating layer 113 is formed on the semiconductor layers 35 and 135, and gate electrodes 25 and 125 are formed on the gate insulating layer 113. In the process of forming the gate electrodes 25 and 125, gate lines (not shown) are also formed.

Next, a first interlayer insulating film 115 is formed on the gate electrodes 25 and 125.

Figure 7:
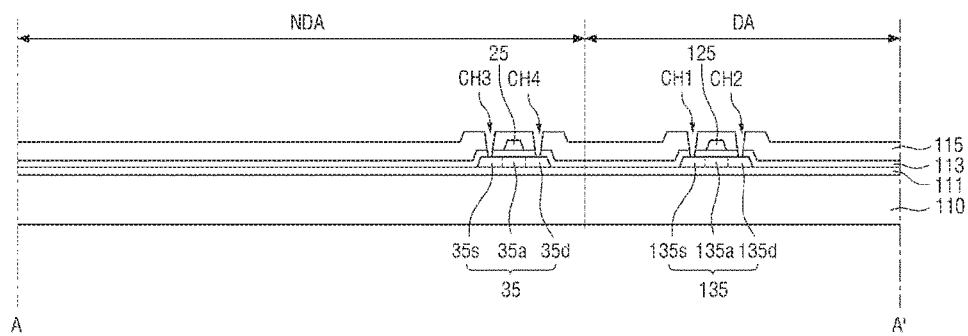

Referring to FIG. 7, a first contact hole CH1 that exposes the source portion 135s of the semiconductor layer 135, a second contact hole CH2 that exposes the drain portion 135d of the semiconductor layer 135, a third contact hole CH3 that exposes the source portion 35s of the semiconductor layer 35 and a fourth contact hole CH4 that exposes the drain portion 35d of the semiconductor layer 35 are formed in the first interlayer insulating film 115 and the gate insulating layer 113.

Figure 8:
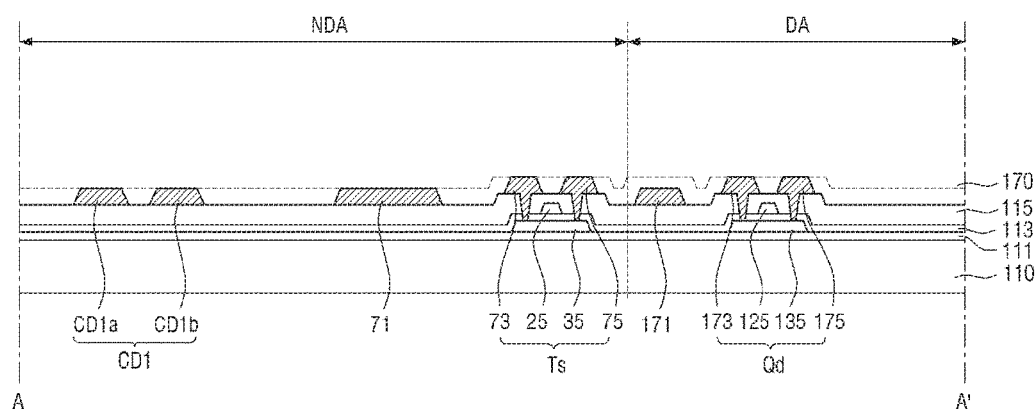

Referring to FIG. 8, a data metal layer 170 is deposited on the first interlayer insulating film 115 and patterned to form source electrodes 73 and 173, drain electrodes 75 and 175, a data line 171, a power supply line 71, and a first crack detection line CD1 including a first line CD1a and a second line CD1b. The source electrode 173 is connected to the semiconductor layer 135 via the first contact hole CH1, the drain electrode 175 is connected to the semiconductor layer 135 via the second contact hole CH2, the source electrode 73 is connected to the semiconductor layer 35 via the third contact hole CH3, and the drain electrode 75 is connected to the semiconductor layer 35 via the fourth contact hole CH4. As a result, a driving thin-film transistor Qd and a circuit thin-film transistor Ts are formed.

Although not illustrated in the drawings, if a second crack detection line CD2 (see FIG. 1) is further provided, it may be formed in the process of forming the first crack detection line CD1.

Figure 9:
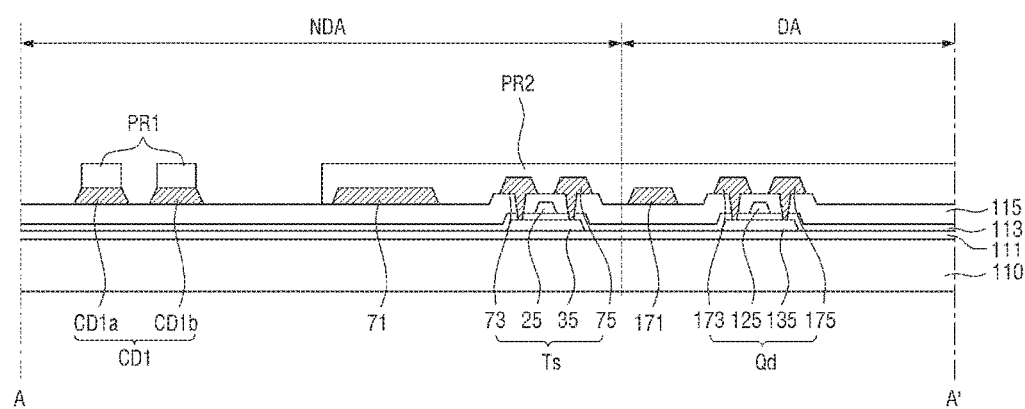

Next, referring to FIG. 9, a first photoresist pattern PR1 and a second photoresist pattern PR2 are formed. The first photoresist pattern PR1 is formed on the first crack detection line CD1 and exposes side surfaces of the first line CD1a and the second line CD1b of the first crack detection line CD1. The second photoresist pattern PR2 completely covers the power supply line 71, the circuit thin-film transistor Ts, the data line 171 and the driving thin-film transistor Qd. In particular, the second photoresist pattern PR2 covers the source electrodes 73 and 173, the drain electrodes 75 and 175, the data line 171 and the power supply line 71, such that their side surfaces are not exposed.

Figure 10:
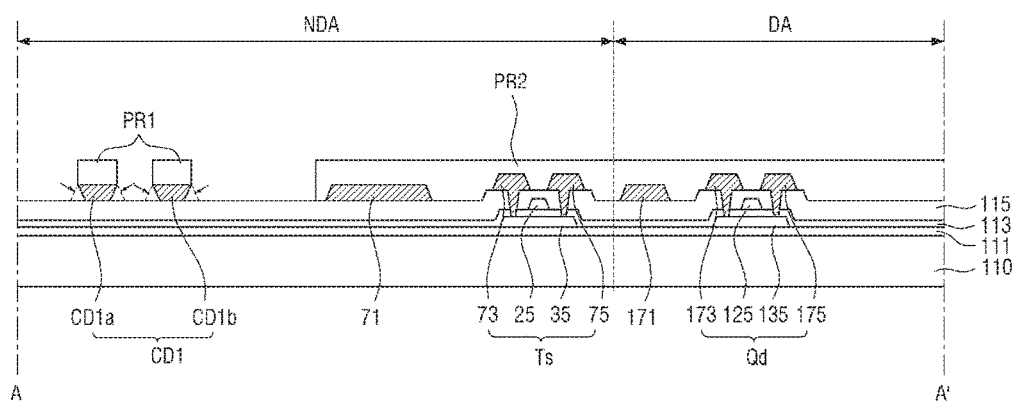

Referring to FIG. 10, the side surfaces of the first line CD1a and the side surfaces of the second line CD1b are etched using the first photoresist pattern PR1 as a mask. Accordingly, each of the first line CD1a and the second line CD1b has an inversely tapered cross-sectional shape.

Figure 11:
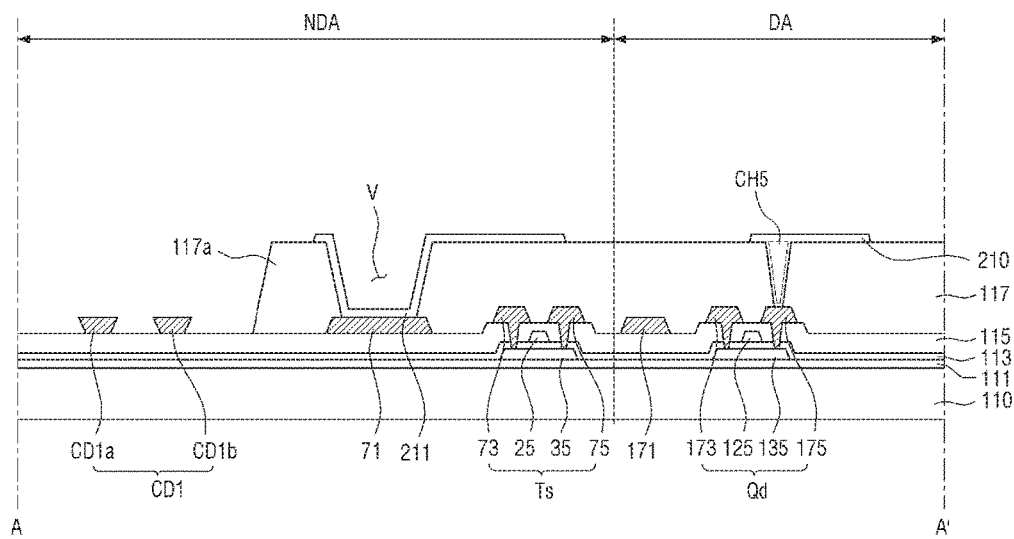

Next, the first photoresist pattern PR1 and the second photoresist pattern PR2 are removed to form a second interlayer insulating film 117 and a first pattern 117a as illustrated in FIG. 11. The second interlayer insulating film 117 may be formed on the driving thin-film transistor Qd and the circuit thin-film transistor Ts, and a fifth contact hole CH5 exposing the drain electrode 175 of the driving thin-film transistor Qd may be formed in the second interlayer insulating film 117. The second interlayer insulating film 117 and the first pattern 117a may be formed by coating a photosensitive organic material on the first interlayer insulating film 115 and exposing and developing the photosensitive organic material. The second interlayer insulating film 117 and the first pattern 117a may be separated from each other with the power supply line 71 interposed between them. A valley V may be formed between the second interlayer insulating film 117 and the first pattern 117a to partially expose the power supply line 71.

Next, a conductive material is deposited on the second interlayer insulating film 117 and patterned to form a first electrode 210 and a connection electrode 211. The first electrode 210 may be connected to the drain electrode 175 via the fifth contact hole CH5, and the connection electrode 211 may be connected to the power supply line 71 via the valley V.

In some embodiments, the process of covering the first crack detection line CD1 with a photoresist pattern may be performed before the conductive material is deposited.

Figure 12:
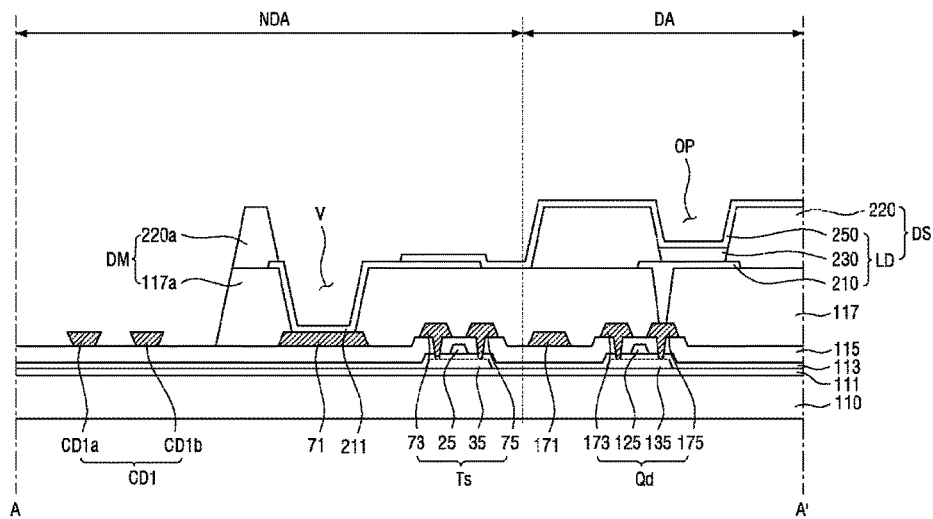

Referring to FIG. 12, a pixel defining layer 220 and a second pattern 220a are formed. The pixel defining layer 220 may be formed on the second interlayer insulating film 117 and may include an opening OP that exposes part of the first electrode 210. The second pattern 220a may be formed on the first pattern 117a to form a dam DM. In some embodiments, the pixel defining layer 220 and the second pattern 220a may be formed by coating a photosensitive organic material and exposing and developing the photosensitive organic material.

A light emitting layer 230 is formed on the first electrode 210 exposed through the opening OP, and a second electrode 250 is formed on the light emitting layer 230 and the pixel defining layer 220. The second electrode 250 may be connected to the connection electrode 211 by partially extending to the connection electrode 211 as described above. The first electrode 210, the light emitting layer 230 and the second electrode 250 may form an OLED LD, and the OLED LD and the pixel defining layer 220 may form a display structure DS.

Figure 13:
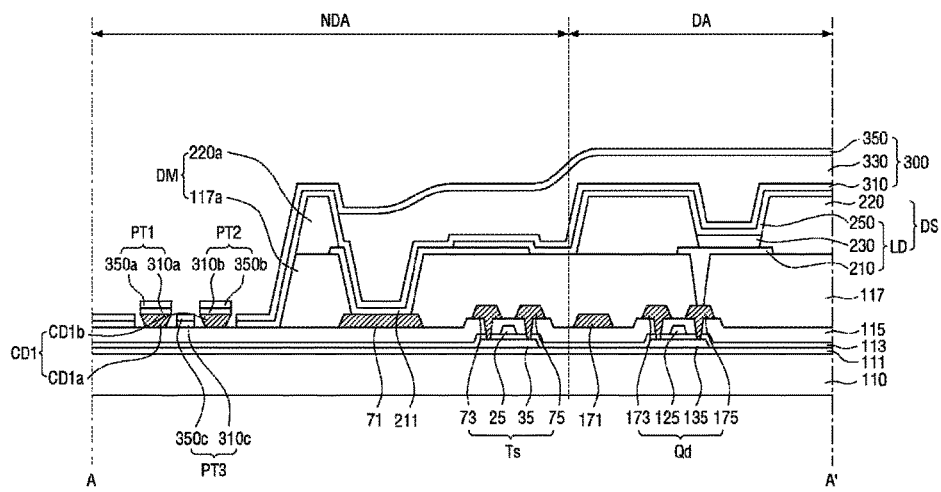
Figure 14:
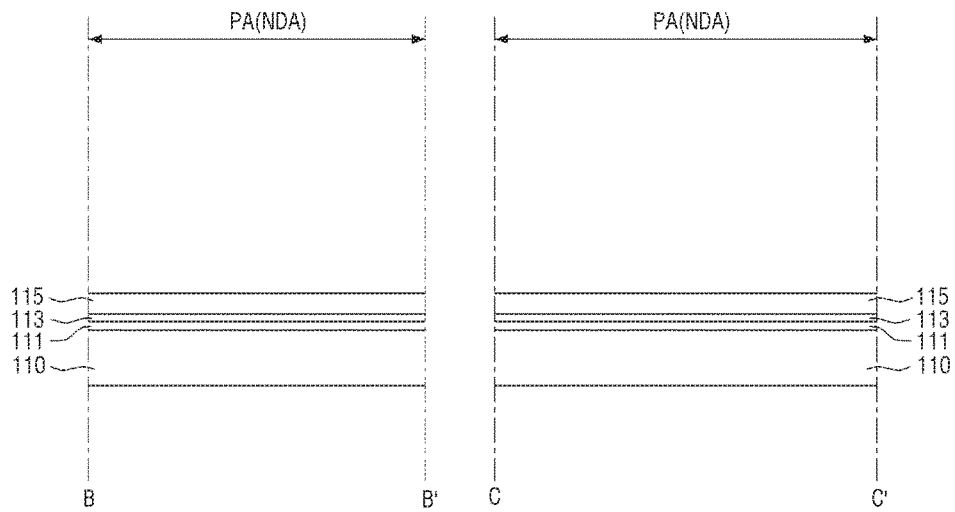
FIGS. 14, 15, 16, 17 and 18 are cross-sectional views illustrating the process of manufacturing the portion of FIG. 5.

Referring to FIG. 13, a thin-film encapsulating layer 300 is formed to encapsulate the OLED LD or the display structure DS. In some embodiments, the thin-film encapsulation layer 300 may have a structure in which a first inorganic film 310, an organic film 330, and a second inorganic film 350 are sequentially stacked on the second electrode 250. In the process of forming the thin-film encapsulation layer 300, a first inorganic film pattern PT1 may be formed on the first line CD1a, a second inorganic film pattern PT2 may be formed on the second line CD1b, and a third inorganic film pattern PT3 may be formed between the first line CD1a and the second line CD1b. Since the first inorganic film pattern PT1, the second inorganic film pattern PT2 and the third inorganic film pattern PT3 are identical to those described above with reference to FIG. 4, they will not be described in detail.

Through the above process, the structure illustrated in FIG. 4 can be manufactured.

FIGS. 14 through 18 are cross-sectional views illustrating the process of manufacturing the portion of FIG. 5.

Referring to FIGS. 5 and 14 through 18, a buffer layer 111, a gate insulating layer 113, and a first interlayer insulating film 115 are sequentially formed on a base layer 110 in a pad area PA. The process of forming the buffer layer 111, the gate insulating layer 113 and the first interlayer insulating film 115 can be performed at substantially the same time as the process illustrated in FIG. 6.

Figure 15:
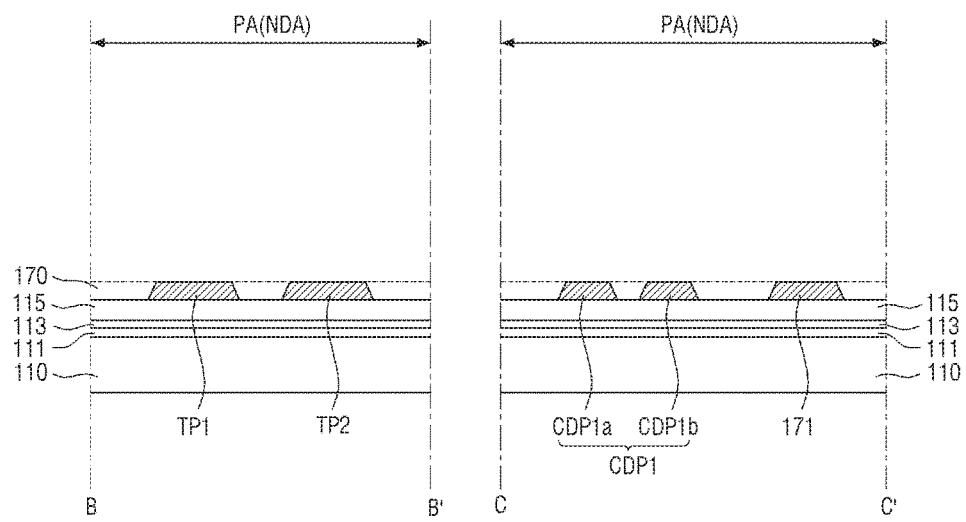

Next, referring to FIG. 15, a data metal layer 170 is deposited on the first interlayer insulating film 115 and patterned to form a first test pad TP1, a second test pad TP2, a first crack detection pattern CDP1 including a first pattern CDP1a and a second pattern CDP1b, and a data line 171. The process of forming the first test pad TP1, the second test pad TP2, the first crack detection pattern CDP1 including the first pattern CDP1a and the second pattern CDP1b, and the data line 171 may be performed at substantially the same time as the process of forming the source electrodes 73 and 173 (see FIG. 8), the drain electrodes 75 and 175 (see FIG. 8), the first crack detection line CD1 (see FIG. 8) and the power supply line 71 (see FIG. 8). Although not illustrated in the drawings, a fifth test pad TP11 (see FIG. 1) and a sixth test pad TP12 may also be formed. In addition, although not illustrated in the drawings, if a second crack detection pattern CDP2 (see FIG. 1) is further provided, it may be formed in the process of forming the first crack detection pattern CDP1.

Figure 16:
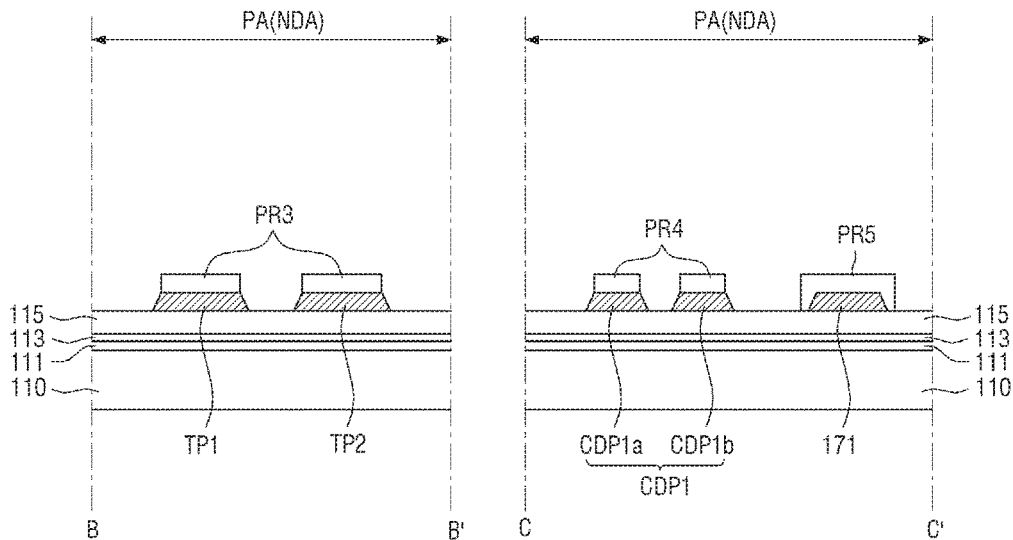
Figure 17:
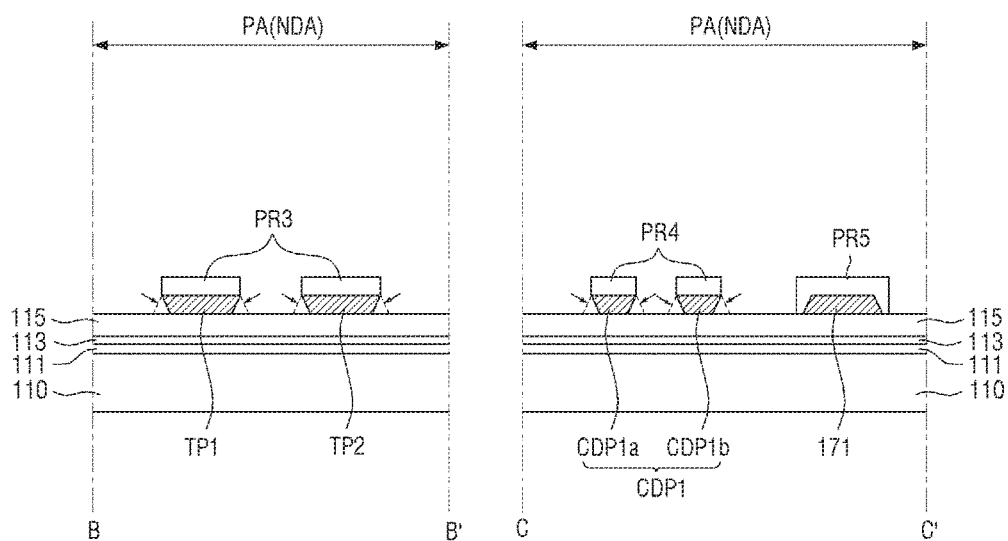

Next, referring to FIG. 16, a third photoresist pattern PR3, a fourth photoresist pattern PR4, and a fifth photoresist pattern PR5 are formed. The third photoresist pattern PR3 may be formed on the first test pad TP1 and the second test pad TP2, and side surfaces of the first test pad TP1 and the second test pad TP2 may be exposed without being covered by the third photoresist pattern PR3. The fourth photoresist pattern PR4 may be formed on the first crack detection pattern CDP1, and side surfaces of the first pattern CDP1a and the second pattern CDP1b may be exposed without being covered by the fourth photoresist pattern PR4. The fifth photoresist pattern PR5 may be formed on the data line 171 in the pad area PA to cover side surface of the data line 171.

The third photoresist pattern PR3, the fourth photoresist pattern PR4 and the fifth photoresist pattern PR5 may be formed at the same time as the first photoresist pattern PR1 (see FIG. 9) and the second photoresist pattern PR2 (see FIG. 9).

Referring to 17, the side surfaces of the first test pad TP1, the side surfaces of the second test pad TP2, the side surfaces of the first pattern CDP1a and the side surfaces of the second pattern CDP1b are etched using the third photoresist pattern PR3 and the fourth photoresist pattern PR4 as a mask. Accordingly, each of the first test pad TP1, the second test pad TP2, the first pattern CDP1a, and the second pattern CDP1b has an inversely tapered shape.

Next, the third photoresist pattern PR3, the fourth photoresist pattern PR4, and the fifth photoresist pattern PR5 are removed.

Figure 18:
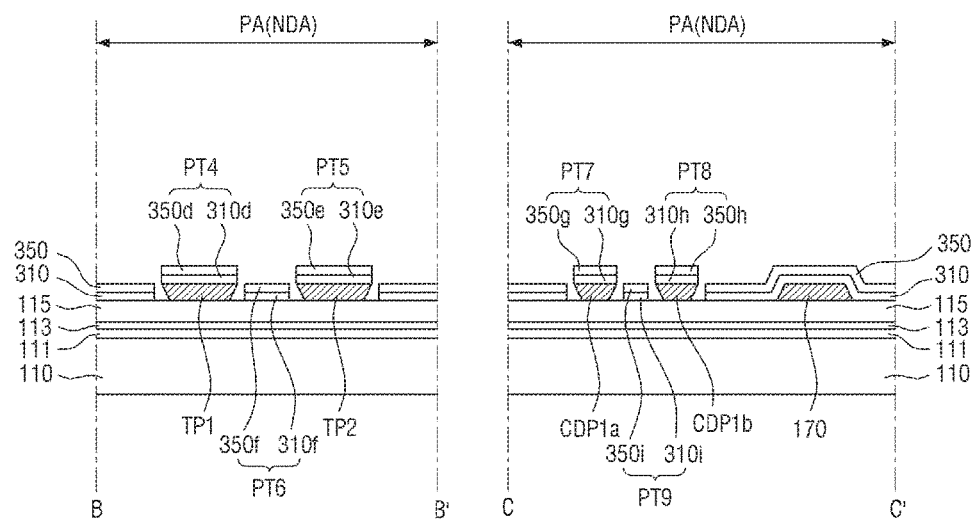

In some embodiments, in the process of forming the thin-film encapsulation layer 300 described above with reference to FIG. 13, a first inorganic film 310 and a second inorganic film 350 of a thin-film encapsulation layer 300 may also be formed in the pad area PA as illustrated in FIG. 18, and an organic film 330 (see FIG. 13) of the thin-film encapsulation layer 300 may be blocked by a dam DM (see FIG. 13).

Accordingly, a fourth inorganic film pattern PT4 may be formed on the first test pad TP1, a fifth inorganic film pattern PT5 may be formed on the second test pad TP2, and a sixth inorganic film pattern PT6 may be formed between the first test pad TP1 and the second test pad TP2. In addition, a seventh inorganic film pattern PT7 may be formed on the first pattern CDP1a, an eighth inorganic film pattern PT8 may be formed on the second pattern CDP1b, and a ninth inorganic film pattern PT9 may be formed between the first pattern CDP1a and the second pattern CDP1b. The inorganic film patterns PT4 through PT9 in the pad area PA may be simultaneously formed in the process of forming the thin-film encapsulation layer 300 (see FIG. 13). The fourth through ninth inorganic film patterns PT4 through PT9 may respectively include lower inorganic film patterns 310d through 310i made of the same material as the first inorganic film 310 and upper inorganic film patterns 350d through 350i made of the same material as the second inorganic film 350.

After the process of FIGS. 13 and 18, the process of removing the first inorganic film 310, the second inorganic film 350, and the inorganic film patterns PT4 through PT9 located in the pad area PA may further be performed. The result is the structure illustrated in FIG. 5. The process of removing the first inorganic film 310, the second inorganic film 350 and the inorganic film patterns PT4 through PT9 may be achieved by forming a photoresist pattern to expose the pad area PA and cover the non-display area NDA excluding the pad area PA and the display area DA and removing the first inorganic film 310, the second inorganic film 350 and the inorganic film patterns PT4 through PT9 located in the pad area PA by using the photoresist pattern as a mask.

Figure 19:
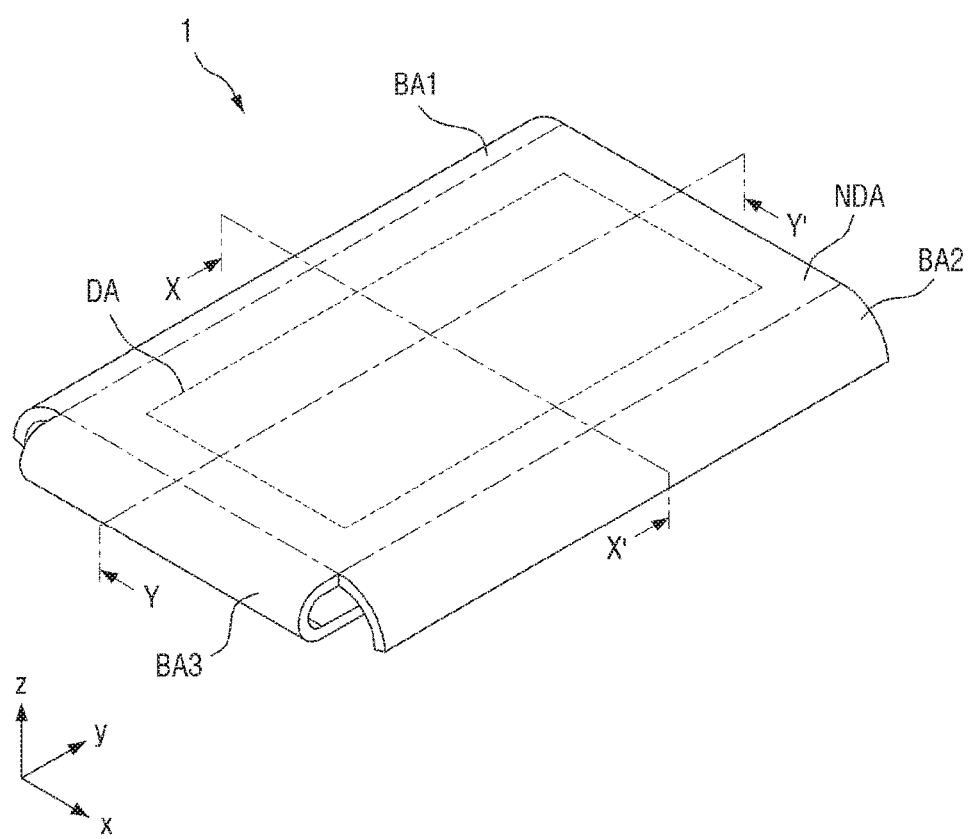
FIG. 19 is a schematic perspective view of the structure of the display device of FIG. 1 in a case where the display device is bent.
Figure 20:
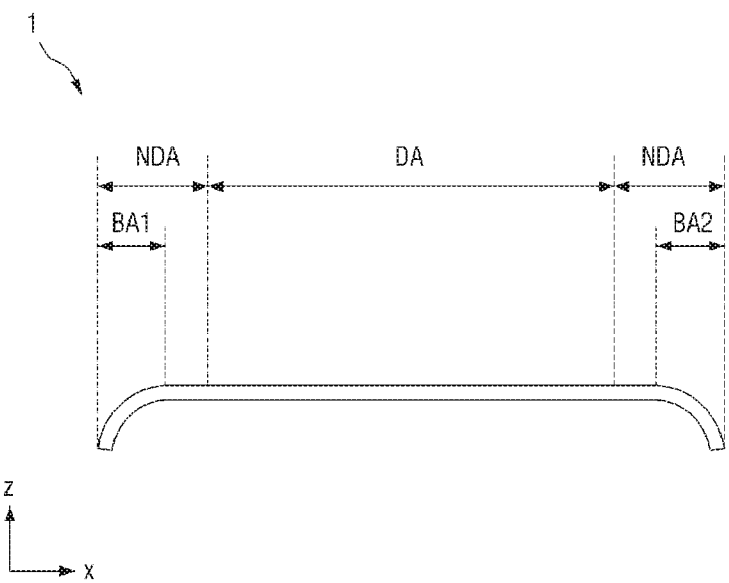
FIG. 20 is a cross-sectional view taken along the line X-X' of FIG. 19.
Figure 21:
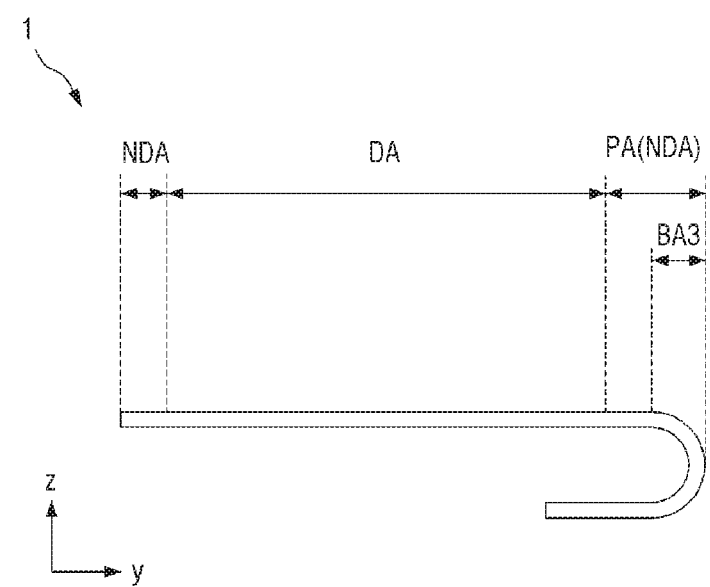
FIG. 21 is a cross-sectional view taken along the line Y-Y' of FIG. 19.

FIG. 19 is a schematic perspective view of the structure of the display device 1 of FIG. 1 in a case in which the display device 1 is bent. FIG. 20 is a cross-sectional view taken along the line X-X' of FIG. 19. FIG. 21 is a cross-sectional view taken along the line Y-Y' of FIG. 19.

Referring to FIGS. 1 and 19 through 21, the display device 1 according to the current embodiment may be at least partially curved or bent.

For example, of the non-display area NDA of the display device 1, an area located on the left side of the display area DA in the drawings may be bent at a predetermined curvature in a downward direction (or a direction opposite to a z-direction) of the display device 1 to form a first bending area BA1. In addition, an area of the non-display area NDA that is located on the right side of the display area DA in the drawings may be bent at a predetermined curvature in the downward direction (or the direction opposite to the z-direction) of the display device 1 to form a second bending area BA2. Also, the pad area PA (see FIG. 1) of the non-display area NDA may be bent at a predetermined curvature in the downward direction of the display device 1 to form a third bending area BA3.

The first crack detection line CD1 (see FIG. 1) described above may extend in the first bending area BA1 of the display device 1 along the first direction y to detect cracks in the first bending area BA1. In addition, the second crack detection line CD2 (see FIG. 1) described above may extend in the second bending area BA2 of the display device 1 along the first direction y to detect cracks in the second bending area BA2. The first crack detection pattern CDP1 (see FIG. 1) and the second crack detection pattern CDP2 (see FIG. 1) may detect cracks in the third bending area BA3.

Figure 22:
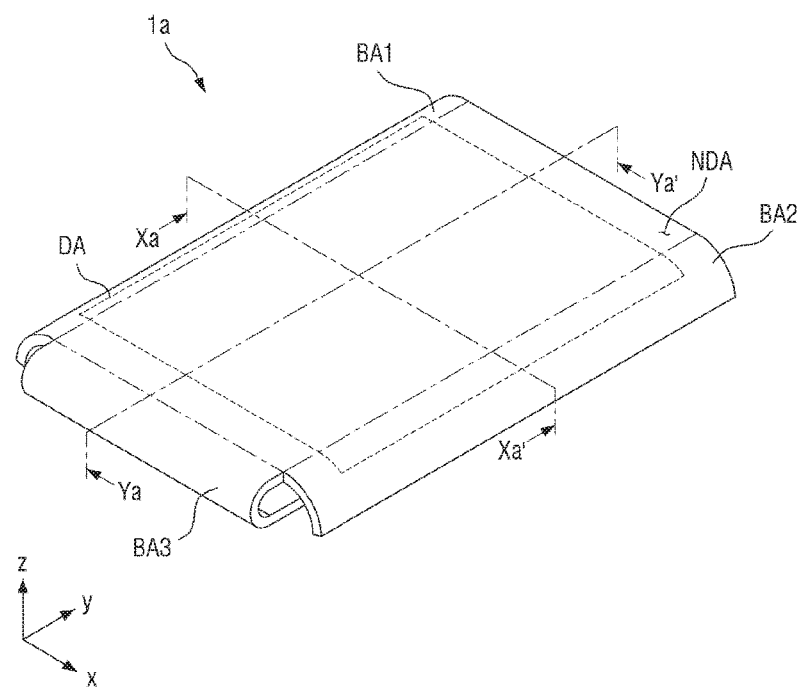
FIG. 22 is a schematic perspective view of the structure of a modified embodiment of the display device illustrated in FIG. 19.
Figure 23:
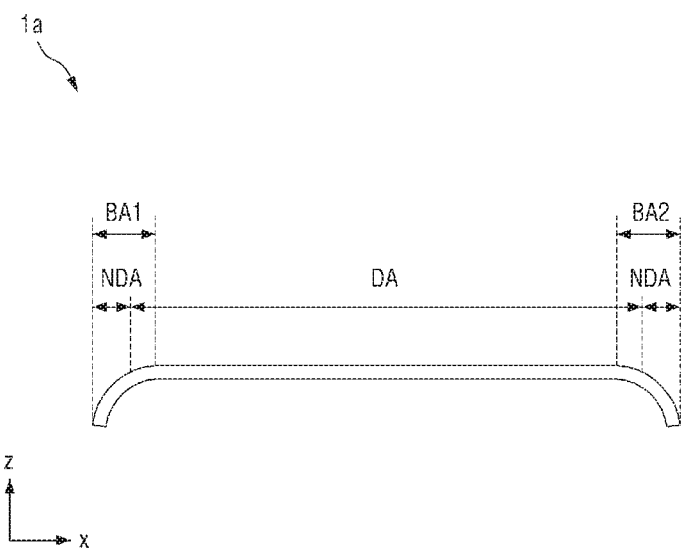
FIG. 23 is a cross-sectional view taken along the line Xa-Xa' of FIG. 22.
Figure 24:
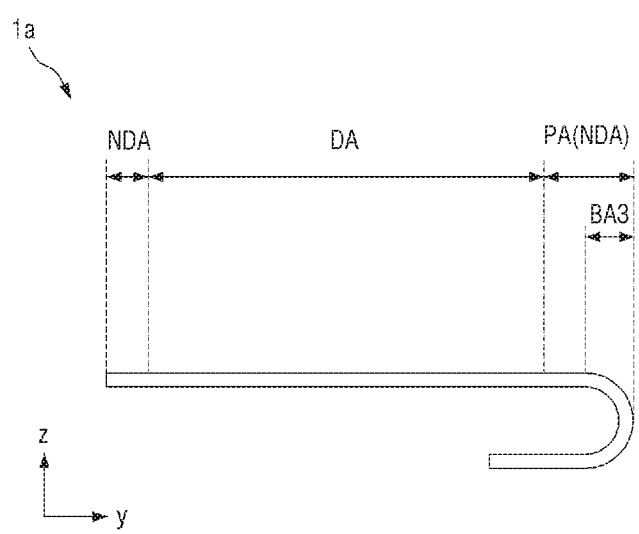
FIG. 24 is a cross-sectional view taken along the line Ya-Ya' of FIG. 22.

FIG. 22 is a schematic perspective view of the structure of a modified embodiment of the display device 1 illustrated in FIG. 19. FIG. 23 is a cross-sectional view taken along the line Xa-Xa' of FIG. 22. FIG. 24 is a cross-sectional view taken along the line Ya-Ya' of FIG. 22.

Referring to FIGS. 22 through 24, a display device 1a according to the current embodiment may be substantially the same as the display device 1 illustrated in FIGS. 19 through 21 except that part of a display area DA is included in each of a first bending area BA1 and a second bending area BA2.

The first crack detection line CD1 (see FIG. 1) may extend in a non-display area NDA of the first bending area BA1 of the display device 1a along the first direction y to detect cracks in the first bending area BA1. In addition, the second crack detection line CD2 (see FIG. 1) may extend in the non-display area NDA of the second bending area BA2 of the display device 1a along the first direction y to detect cracks in the second bending area BA2. The first crack detection pattern CDP1 (see FIG. 1) and the second crack detection pattern CDP2 (see FIG. 1) may detect cracks in the third bending area BA3.

In FIGS. 22 through 24, part of the display area DA is included in each of the first bending area BA1 and the second bending area BA2. However, this is merely an example. That is, in some embodiments, part of the display area DA may be included in the first bending area BA1 but may not be included in the second bending area BA2.

Figure 25:
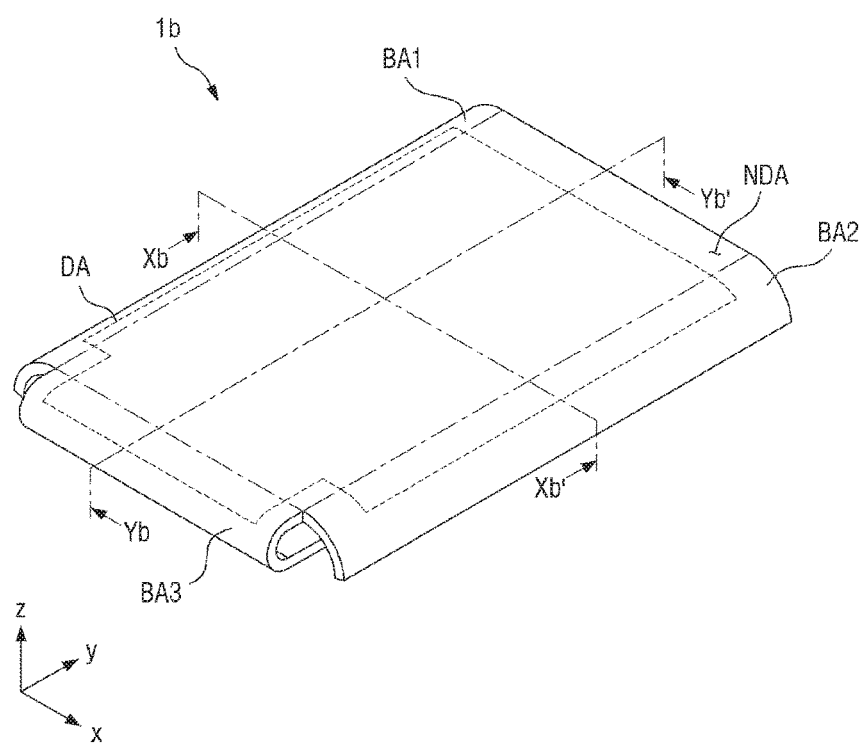
FIG. 25 is a schematic perspective view of the structure of a modified embodiment of the display device illustrated in FIG. 19.
Figure 26:
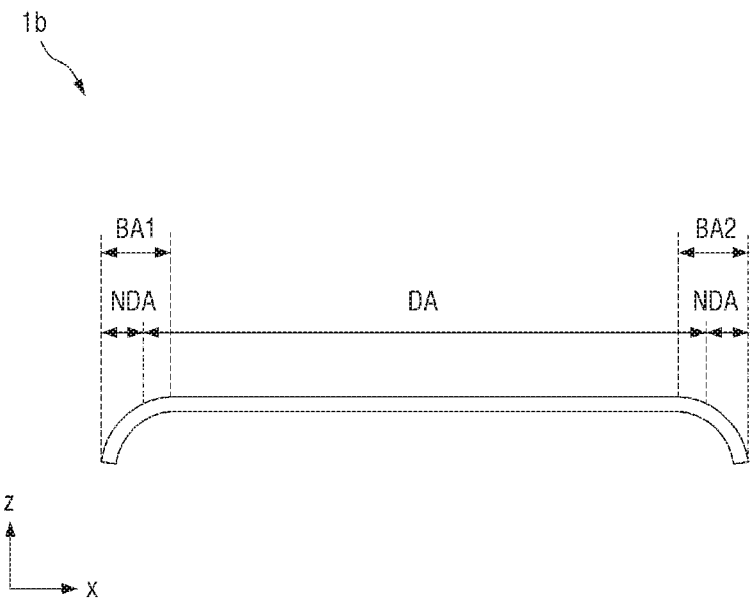
FIG. 26 is a cross-sectional view taken along the line Xb-Xb' of FIG. 25.
Figure 27:
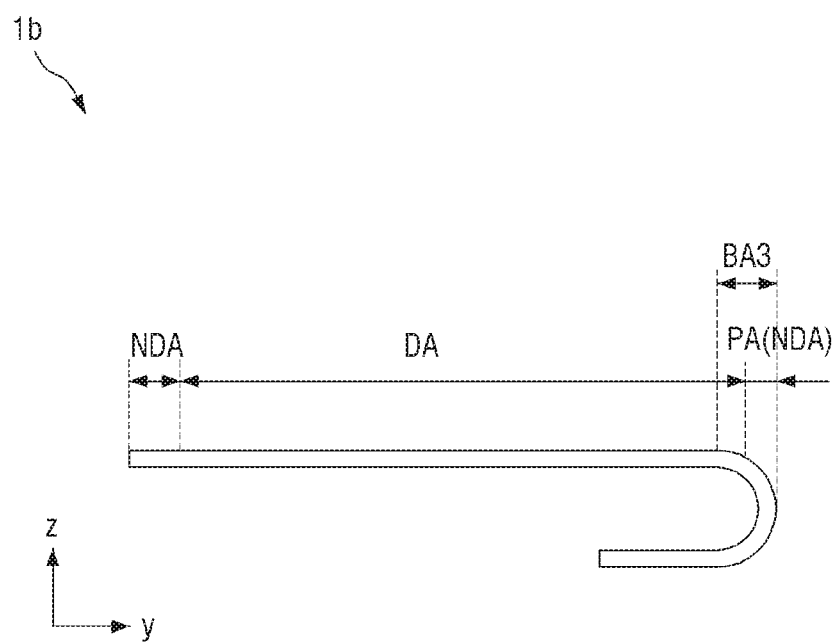
FIG. 27 is a cross-sectional view taken along the line Yb-Yb' of FIG. 25.

FIG. 25 is a schematic perspective view of the structure of a modified embodiment of the display device 1 illustrated in FIG. 19. FIG. 26 is a cross-sectional view taken along the line Xb-Xb' of FIG. 25. FIG. 27 is a cross-sectional view taken along the line Yb-Yb' of FIG. 25.

FIGS. 25 through 27, a display device 1b according to the current embodiment may be substantially the same as the display device 1 illustrated in FIGS. 19 through 21 except that part of a display area DA is included in each of a first bending area BA1, a second bending area BA2 and a third bending area BA3.

Referring to FIGS. 25 through 27, part of the display area DA is included in each of the first bending area BA1, the second bending area BA2 and the third bending area BA3. However, this is merely an example. That is, in some embodiments, part of the display area DA may be included in the third bending area BA3 but may not be included in the first bending area BA1 and the second bending area BA2. Alternatively, part of the display area DA may be included in the third bending area BA3 and any one of the first bending area BA1 and the second bending area BA2.

The first crack detection line CD1 (see FIG. 1) may detect cracks in the first bending area BA1 of the display device 1b, and the second crack detection line CD2 (see FIG. 1) may detect cracks in the second bending area BA2 of the display device 1b. In addition, the first crack detection pattern CDP1 (see FIG. 1) and the second crack detection pattern CDP2 (see FIG. 1) may detect cracks in the third bending area BA3.

According to an embodiment, cracks in a display device can be easily detected. Therefore, defects of the display device due to cracks can be prevented.

However, the effects of the inventive concept are not restricted to the one set forth herein. The above and other effects of the inventive concept will become more apparent to one of daily skill in the art to which the inventive concept pertains by referencing the claims.

What is claimed is:

1. A display device comprising:
   a display area and a non-display area located around the display area;
   a base layer;
   an organic light-emitting diode (OLED) that is located on the base layer in the display area; and
   a first crack detection line that is located on the base layer in the non-display area;
   wherein the first crack detection line comprises a first line that extends substantially in a first direction along a first edge of the display area, a second line that is separated from the first line and extends substantially in the first direction, and a third line that is connected to an end of the first line and an end of the second line, wherein a cross-sectional shape of the entire first line in a second direction crossing the first direction is inversely tapered.

2. The display device of claim 1, wherein a shortest distance between the first crack detection line and an edge of the base layer is 50 µm to 100 µm.

3. The display device of claim 1, wherein a cross-sectional shape of the second line in the second direction is inversely tapered.

4. The display device of claim 1, further comprising:
   a first test pad that is located in the non-display area and connected to the other end of the first line; and
   a second test pad that is located in the non-display area and connected to the other end of the second line.

5. The display device of claim 4, wherein a cross-sectional shape of the first test pad or a cross-sectional shape of the second test pad is inversely tapered.

6. The display device of claim 5, further comprising a thin-film encapsulation layer that seals the OLED, wherein the first test pad and the second test pad do not contact the thin-film encapsulation layer.

7. The display device of claim 1, further comprising a second crack detection line that is located on the base layer in the non-display area and separated from the first crack detection line, wherein the second crack detection line comprises a fourth line that extends substantially in the first direction along a second edge of the display area that faces the first edge, a fifth line that is separated from the fourth line and extends substantially in the first direction, and a sixth line that is connected to an end of the fourth line and an end of the fifth line, wherein a cross-sectional shape of the fourth line in the second direction crossing the first direction is inversely tapered.

8. The display device of claim 7, wherein a cross-sectional shape of the fifth line in the second direction is inversely tapered.

9. The display device of claim 1, further comprising:
   a semiconductor layer that is located on the base layer in the display area;
   a gate insulating layer that is located on the base layer and the semiconductor layer;
   a gate electrode that is located on the gate insulating layer;
   a first interlayer insulating film that is located on the gate electrode and the gate insulating layer; and
   a source electrode and a drain electrode that are located on the first interlayer insulating film,
   wherein the first crack detection line is located on the first interlayer insulating film and made of the same material as the source electrode and the drain electrode.

10. The display device of claim 1, further comprising a power supply line that is located on the base layer in the non-display area and positioned between the display area and the first crack detection line.

11. The display device of claim 10, further comprising:
    a semiconductor layer that is located on the base layer in the display area;
    a gate insulating layer that is located on the base layer and the semiconductor layer;
    a gate electrode that is located on the gate insulating layer;

a first interlayer insulating film that is located on the gate electrode and the gate insulating layer; and a source electrode and a drain electrode that are located on the first interlayer insulating film, wherein the power supply line is located on the first interlayer insulating film and made of the same material as the source electrode and the drain electrode.

12. The display device of claim 11, wherein the first crack detection line is made of the same material as the power supply line.

13. The display device of claim 11, further comprising a second interlayer insulating film that is located on the source electrode and the drain electrode, wherein the OLED comprises a first electrode that is located on the second interlayer insulating film and connected to the drain electrode, a light emitting layer that is located on the first electrode, and a second electrode that is located on the light emitting layer, wherein the second electrode is electrically connected to the power supply line.

14. The display device of claim 13, further comprising a connection electrode that contacts the power supply line and the second electrode and is made of the same material as the first electrode, wherein the second electrode is connected to the power supply line by the connection electrode.

15. The display device of claim 1, further comprising a dam that is located on the base layer and positioned in the non-display area between the display area and the first crack detection line.

16. The display device of claim 15, further comprising:
a thin-film transistor that is located on the base layer in the display area;
an interlayer insulating film that is located on the thin-film transistor; and
a pixel defining layer that is located on the interlayer insulating film and comprises an opening,
wherein the OLED comprises a first electrode that is located on the interlayer insulating film, electrically connected to the thin-film transistor and at least partially exposed through the opening, a light emitting layer that is located on the first electrode, and a second electrode that is located on the light emitting layer, wherein the dam comprises a first pattern which is made of the same material as the interlayer insulating film and a second pattern that is located on the first pattern and made of the same material as the pixel defining layer.

17. The display device of claim 16, further comprising a thin-film encapsulation layer that seals the OLED and comprises an inorganic film and an organic film, wherein the organic film is located inside the dam.

18. The display device of claim 16, further comprising a thin-film encapsulation layer that seals the OLED and comprises a first inorganic film, a second inorganic film, and an organic film located between the first inorganic film and the second inorganic film, wherein the first inorganic film and the second inorganic film contact each other on the outside of the dam.

19. The display device of claim 18, further comprising an inorganic film pattern that is located on the first line, wherein the inorganic film pattern is separated from the first inorganic film and the second inorganic film.

20. The display device of claim 19, wherein the inorganic film pattern comprises the same material as the first inorganic film or the second inorganic film.

21. The display device of claim 1, further comprising:
a first inorganic film pattern disposed directly on the first line; and
a second inorganic film pattern disposed directly on the second line,
wherein the first inorganic film pattern and the second inorganic film pattern are spaced apart from each other in the second direction.

22. The display device of claim 1, further comprising:
an inorganic film pattern disposed between the first line and the second line;
wherein the inorganic film pattern, the first line and the second line are spaced apart from each other in the second direction.

23. A display device comprising:
a display area and a non-display area located around the display area;
a base layer;
a thin-film transistor that is located on the base layer in the display area;
a pad which is located on the base layer in the non-display area;
a data line that is located on the base layer, extends substantially in a first direction, is electrically connected to the thin-film transistor in the display area, and is electrically connected to the pad in the non-display area; and
a crack detection pattern that is located between an edge of the base layer and the data line in the non-display area and separated from the data line,
wherein a cross-sectional shape of the entire crack detection line in a second direction crossing the first direction is inversely tapered.

24. The display device of claim 23, wherein the crack detection pattern comprises a first pattern that extends substantially in the first direction, a second pattern that is separated from the first pattern and extends substantially in the first direction, and a connection pattern that connects the first pattern and the second pattern, wherein a cross-sectional shape of the first pattern in the second direction is inversely tapered.

25. The display device of claim 24, wherein a cross-sectional shape of the second pattern in the second direction is inversely tapered.

26. The display device of claim 23, further comprising:
an interlayer insulating film that is located on the thin-film transistor;
an OLED that is located on the interlayer insulating film and electrically connected to the thin-film transistor; and
a thin-film encapsulation layer that is located on the OLED and seals the OLED,
wherein the crack detection pattern does not contact the thin-film encapsulation layer.

* * * * *